(12) United States Patent
Mandelis et al.

(10) Patent No.: US 11,231,358 B2
(45) Date of Patent: Jan. 25, 2022

(54) SYSTEMS AND METHODS FOR PERFORMING ENHANCED TRUNCATED-CORRELATION PHOTOTHERMAL COHERENCE TOMOGRAPHY

(71) Applicants: Andreas Mandelis, Scarborough (CA); Koneswaran S. Sivagurunathan, Scarborough (CA); Pantea Tavakolian, Etobicoke (CA)

(72) Inventors: Andreas Mandelis, Scarborough (CA); Koneswaran S. Sivagurunathan, Scarborough (CA); Pantea Tavakolian, Etobicoke (CA)

(*) Notice: Subject to any disclaimer, the term of this patent is extended or adjusted under 35 U.S.C. 154(b) by 0 days.

(21) Appl. No.: 16/900,471

(22) Filed: Jun. 12, 2020

(65) Prior Publication Data

US 2021/0389234 A1    Dec. 16, 2021

(51) Int. Cl.
| | |
|---|---|
| *A61B 5/01* | (2006.01) |
| *G01N 21/17* | (2006.01) |
| *G06T 11/00* | (2006.01) |
| *A61B 5/00* | (2006.01) |

(52) U.S. Cl.
CPC ......... *G01N 21/171* (2013.01); *A61B 5/0093* (2013.01); *A61B 5/015* (2013.01); *A61B 5/4312* (2013.01); *G06T 11/003* (2013.01); *A61B 2576/00* (2013.01); *G01N 2021/1714* (2013.01)

(58) Field of Classification Search
CPC ..... A61B 5/0093; A61B 5/015; A61B 5/4312; A61B 2576/00; G01N 21/171; G01N 2021/1714; G06T 11/003
See application file for complete search history.

(56) References Cited

U.S. PATENT DOCUMENTS

| | | |
|---|---|---|
| 9,220,415 B2 | 12/2015 | Mandelis et al. |
| 9,584,771 B2 | 2/2017 | Mandelis et al. |
| 9,810,650 B2 | 11/2017 | Mandelis et al. |

*Primary Examiner* — Mark R Gaworecki
(74) *Attorney, Agent, or Firm* — Hill & Schumacher

(57) ABSTRACT

Systems and methods are provided for performing thermophotonic imaging using cross-correlation and subsequent time-gated truncation. Photothermal radiation is detected with an infrared camera while exciting a sample with a chirped set of incident optical pulses and time-dependent photothermal signal data is processed using a method that involves performing cross-correlation and subsequent time-gated truncation. The post-cross-correlation truncation method results in depth-resolved images with axial and lateral resolution beyond the well-known thermal-diffusion-length-limited, depth-integrated nature of conventional imaging modalities. An axially resolved photothermal image sequence can be obtained, capable of reconstructing three-dimensional visualizations of photothermal features in wide classes of materials.

15 Claims, 17 Drawing Sheets
(12 of 17 Drawing Sheet(s) Filed in Color)

SYSTEMS AND METHODS FOR PERFORMING ENHANCED TRUNCATED-CORRELATION PHOTOTHERMAL COHERENCE TOMOGRAPHY

BACKGROUND

The present disclosure relates to thermal imaging. More particularly, the present disclosure relates to the nondestructive characterization of objects and materials.

Laser-induced photothermal imaging (also known as "active thermography" in the field of non-destructive testing) can monitor optical absorption in light scattering tissues significantly deeper than purely optical imaging methods like optical coherence tomography (OCT). Photothermal effects use optical-to-thermal energy conversion to generate thermal images which, in principle, replicate optical absorption profiles and/or thermophysical property variations in materials and tissues. photothermal responses of non-opaque media and biological tissues probed with infrared sensors or cameras produce thermophotonic images (i.e. through thermal infrared photon emission from optical-source-irradiated targets as a result of elevated temperature due to optical absorption and non-radiative conversion to heat), with optical property (visible/near-IR absorption and mid-IR emission coefficient) contrast amplified by concurrent thermal property contrast (thermal diffusivity variations). For example, biothermophotonic images resolve minute differences in optical absorption coefficients of blood-rich oxygenated or hypoxic highly optically scattering tissues and their contrast from each other and from blood-deficient (hypoxic) surroundings.

SUMMARY

In various embodiments of the present disclosure, photothermal radiation is detected with an infrared camera while exciting a sample with a chirped set of incident optical pulses and time-dependent photothermal signal data is processed using a method that involves performing cross-correlation and subsequent time-gated truncation. The post-cross-correlation truncation method results in depth-resolved images with axial and lateral resolution beyond the well-known thermal-diffusion-length-limited, depth-integrated nature of conventional imaging modalities. An axially resolved photothermal image sequence can be obtained, capable of reconstructing three-dimensional visualizations of photothermal features in wide classes of materials.

Accordingly, in a first aspect, there is provided a method of performing photothermal imaging, the method comprising:
employing an excitation chirped waveform to generate a chirped sequence of optical pulses;
a) directing the chirped sequence of optical pulses onto a sample;
b) detecting, with an infrared camera, photothermal radiation emitted from the sample, thereby obtaining time-dependent photothermal signal data for each image pixel of the infrared camera;
c) employing the excitation chirped waveform to provide a reference chirped waveform, the reference chirped waveform comprising a chirped sequence of pulses, wherein each pulse of the reference chirped waveform is delayed by a time delay relative to a corresponding pulse of the excitation chirped waveform;
d) for each pixel of a plurality of pixels of the infrared camera:
cross-correlating a respective time-dependent photothermal signal data with the reference chirped waveform and obtaining respective time-dependent cross-correlation data; and
after having performed the cross-correlation, processing a truncated, time-gated subset of the time-dependent cross-correlation data to generate a cross-correlation measure; and
e) generating image data based on the cross-correlation measures associated with the plurality of pixels.

In some implementations of the method, the reference chirped waveform comprises pulses having a fixed pulse width and a chirped pulse repetition rate.

In some implementations of the method, cross-correlation is performed based on in-phase and quadrature representations of the reference chirped waveform. A temporal duration of the time-gated subset of the time-dependent cross-correlation data may be equal to a difference between a temporal width of a final pulse of the time-dependent photothermal signal data and the time delay.

In some implementations of the method, the cross-correlation measure corresponds to a peak of a time-dependent amplitude of the time-gated subset of the time-dependent cross-correlation data. The cross-correlation measure may comprise one or more of peak amplitude, phase value associated with the peak amplitude, and time value associated with the peak amplitude.

In some implementations of the method, the cross-correlation measure is a phase delay corresponding to a time duration associated with a change in a sign of the phase.

In some implementations of the method, the method further comprises:
varying a wavelength of the chirped sequence of optical pulses; and
repeating steps a) to c) to generate multispectral image data.

In some implementations of the method, the method further comprises:
cross-correlating the time-dependent photothermal signal data with one or more additional reference chirped waveforms, each additional reference chirped waveform having a different associated time delay applied thereto;
generating additional image data respectively corresponding to each additional reference chirped waveform; and
generating volumetric image data based on the image data and the additional image data.

In some implementations of the method, each pulse of the reference chirped waveform has a pulse width less than a pulse width of the pulses of the excitation chirped waveform.

In some implementations of the method, each pulse of the reference chirped waveform has a pulse width exceeding than a pulse width of the pulses of the excitation chirped waveform.

In some implementations of the method, each pulse of the reference chirped waveform has a pulse width that is the same as a pulse width of the pulses of the excitation chirped waveform.

In another aspect, there is provided a method of performing adaptive spatially filtering of a diffusive thermophotonic image, the method comprising:
scanning a resonant gate filter relative to the diffusive thermophotonic image, the resonant gate filter producing a peak when a spatial width of a spatial gate matches a steepest lateral gradient within an absorbing region of the diffusive thermophotonic image; and generating a filtered image according to locations of the identified peaks.

In some implementations of the method, a first filtered image is generated by scanning the resonant gate filter across a first direction, a second filtered image is generated by scanning the resonant gate filter across a second direction, and a composite filtered image is generated based on the first filtered image and the second filtered image.

In another aspect, there is provided a system for performing photothermal imaging, the system comprising:
  a laser;
  an infrared camera; and
  computer hardware comprising at least one processor and associated memory, the memory comprising instructions executable by said at least one processor to perform operations comprising:
    generating an excitation chirped waveform comprising a chirped sequence of pulses;
    controlling the laser according to the excitation chirped waveform, such that the laser emits a chirped sequence of laser pulses onto a sample;
    detecting, with the infrared camera, photothermal radiation emitted from the sample, thereby obtaining time-dependent photothermal signal data for each image pixel of the infrared camera;
    employing the excitation chirped waveform to provide a reference chirped waveform, the reference chirped waveform comprising a chirped sequence of pulses, wherein each pulse of the reference chirped waveform is delayed by a time delay relative to a corresponding pulse of the excitation chirped waveform;
    for each pixel of a plurality of pixels of the infrared camera:
      cross-correlating a respective time-dependent photothermal signal data with the reference chirped waveform and obtaining respective time-dependent cross-correlation data; and
      after having performed the cross-correlation, processing a time-gated subset of the time-dependent cross-correlation data to generate a cross-correlation measure; and
    generating image data based on the cross-correlation measures associated with the plurality of pixels.

A further understanding of the functional and advantageous aspects of the disclosure can be realized by reference to the following detailed description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments will now be described, by way of example only, with reference to the drawings, in which:

FIG. 10A shows the 3D eTC-PCT amplitude image of the mouse thigh before injection of cancer cells and FIG. 10B shows a side view of the thigh with the right corner removed. FIG. 10C shows a 3D eTC-PCT amplitude image of the mouse thigh 3 days after injection of the cancer cells, and FIG. 10D shows a view of the thigh with the right corner removed to reveal the penetration depth of the tumor on day 3 in the tissue. FIG. 10E shows a 3D amplitude image of the mouse thigh 9 days after injection of the cancerous cells, and FIG. 10F shows a 3D view of the thigh with the right corner of the image removed to reveal the penetration depth of the tumor in the tissue. On day 3 tumor size is much smaller than on day 9. The image size is 1.35 cm×1.08 cm, and the depth scale is ~2 mm.

FIGS. 11A and 11B plot the eTC-PCT amplitude and phase images, respectively, at 400 ms. The spatial-gradient-gate adaptive filtered image shown in FIG. 11C, of the combined amplitude and phase images, shows more details such as revealing the presence of smaller vessels. The color bars on the filtered image do not have units as it is derived from mixing amplitude and phase.

DETAILED DESCRIPTION

Figure 1:
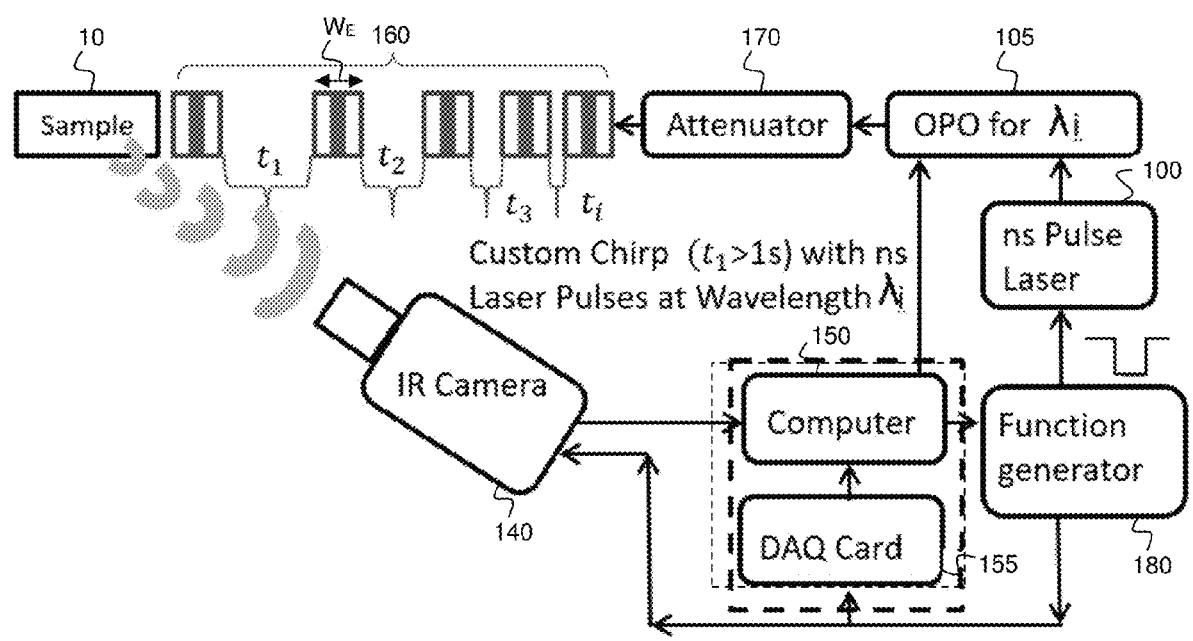
FIG. 1 schematically illustrates an example system for performing multispectral (multi-wavelength) enhanced truncated correlation photothermal coherence tomography (eTC-PCT) thermophotonic three-dimensional imaging using a pulsed ns laser.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure employ systems and methods for performing cross-correlation and subsequent truncation to extract depth-dependent image data from photothermal signals. According to one example method disclosed herein, time-dependent photothermal signal data is obtained by detecting photothermal radiation emitted by a sample while the sample is excited with fixed-width optical pulses having a chirped repetition rate. The detected time-dependent photothermal signal data is processed using a filtering method that employs post-cross-correlation truncation to extract depth-dependent image data from the time-dependent photothermal signal data. This method is henceforth referred to as enhanced truncated-correlation photothermal coherence tomography (eTC-PCT) and various example implementations of the eTC-PCT method are illustrated in the following description and examples.

An example system for performing eTC-PCT is shown in FIG. 1. The example system includes a laser 100 (for example, a pulsed diode laser, which can be driven by laser driver) that emits laser pulses, which are directed onto sample 10 for inducing a photothermal response therein. The laser pulses emitted by laser 100 may be homogenized prior to be directed onto the sample 10, for example, using a beam homogenizer. In some implementations, the laser beam may be passed through a collimator, and a diffuser to become collimated, expanded, and homogenized. The laser pulses emitted by the laser may be guided through a length of optical fiber prior to being directed onto the sample 10.

In some example embodiments, the laser may output pulses in the near-infrared spectral range. In some example implementations, the laser pulses may be generated by a pulsed laser. In other example implementations, the laser pulses may be generated by modulating the output of a continuous wave laser.

In some example implementations, the wavelength of the chirped train of optical pulses may be tunable, thereby facilitating the collection of multispectral data. For example, as shown in FIG. 1, the output of the pulsed laser source 100 may be fed to an optical parametric oscillator 105, which generates a corresponding wavelength-shifted and wavelength-tunable chirped pulse train. For example, a pulsed solid-state laser, such as a Nd:YAG pulsed laser (5 ns FWHM) at fundamental emission wavelength 1064 nm encompassing a second harmonic wavelength (532 nm), may be employed to pump an optical parametric oscillator (OPO) for achieving such tunability.

The laser pulses are absorbed by sample 10, thereby generating a photothermal signal that is radiated by sample 10 and detected via infrared camera 140. Time-dependent photothermal signal data from camera 140 is recorded and processed, by control and processing circuitry 150 (e.g. a computer 152, optionally interfaced through a DAQ card 154, as shown in the non-limiting example figure), in order to extract eTC-PCT image data corresponding to various depths within sample 10. In one example implementation, the camera is a mid-infrared camera, such as the Flir A6700sc which has a 3-5 µm spectral response. Imaging camera 140 may be configured with active lock-in capability to detect "waveform engineered" image time sequences which are further processed to become eTC-PCT tomograms. The infrared camera 140 may be triggered by control and processing circuitry 100 to initiate image frame acquisition following photothermal excitation of the sample.

In order to implement the example eTC-PCT method shown in FIGS. 2A-2D, the pulses emitted by the laser are chirped according to an excitation chirped waveform. For example, the excitation chirped waveform may be provided to a laser driver associated with the laser 100 or to a downstream optical modulator. FIG. 1 illustrates an example and non-limiting method of pulse chirping, in which the pulse profile 160 emitted by laser 100 is generated as a series of pulses with a constant pulse profile $W_E$, but with a chirp in the delay between pulses (i.e. a chirp in the pulse repetition rate). An attenuator 170 may be employed to control an optical intensity of the pulses. In some example embodiments, the chirped delay between successive pulses is at least one second in duration.

As shown in FIG. 1, a function generator 180 may be employed to generate the excitation chirped waveform (the function generator 180) may be integrated with the control and processing circuitry 150). In one example implementation, the excitation pulse chirped waveform that is provided as input (e.g. to the driver) is generated by a function generator.

As shown in FIG. 1, a linear frequency modulated (LFM) train of short optical pulses (E) of pulse width $W_E$ is used to excite the sample. It will be understood that this example excitation chirped waveform, and the example method of generating this excitation chirped waveform, are intended to be provided as non-limiting examples, and that other excitation chirped waveforms and excitation chirped waveform generation methods may be alternatively employed.

A practical example of an implementation of the system shown in FIG. 1 includes a function generator 180 (Keysight 33500B, USA) for generating the linear frequency modulation (LFM), the pulse width being adjustable (although in the present example, the pulse width $W_E$ is fixed). According to the present example, this pulse chirp controls the laser 100 and can be recorded via a high speed data acquisition module (e.g. NI PCI-5122) (interfaced with the control and processing circuitry 150) for synthesizing the reference chirp for post-processing, as described further below. The camera frames are stored with its data acquisition provision.

Furthermore, a new method is proposed in FIG. 1 to construct a pulsed chirp waveform with total chirp time in seconds but local laser ON time for local pulses in the ns range. As shown in FIG. 1, in part 180, a function generator is used to send a pulse with negative polarity to a ns range pulsed laser. Upon receiving a trigger pulse, the laser will emit a pulse with OPO-defined wavelength X. After the user-defined laser-off time $t_i$ following the chirp waveform, the function generator will be programed to send the next pulse. In this manner, the ns range laser can be used to generate pulsed chirps (with user defined start and end frequency and frequency scan rate) with total chirp time in the range of seconds. The camera will be triggered by the same pulse generated by the function generator to capture the photothermal response with maximum camera sampling time in the ms time scale. With this custom designed pulse chirp to excite the laser at a given wavelength, large enough energy will be applied to the test sample to generate photothermal signals from deeply seated absorbers in the probed volume so that diffusing thermal signals from deep subsurface regions can be captured at different delay times of the eTC-PCT signal and the processing algorithm can stack them up with delay time as a parameter to reconstruct the 3D structure of the probed volume with improved axial resolution and depth detection range.

This chirp is effectively encoded into the time-dependent photothermal signal data that is obtained via infrared camera 140, and can be employed, via cross-correlation methods that involve post-cross-correlation truncation, to extract depth-dependent image data. It will be understood that although the example embodiments described herein employ a linear chirp, alternative implementations may be realized using a non-linear chirp.

The eTC-PCT process involves the processing of the detected time-dependent photothermal signal data in order to extract depth-dependent image data. The post processing is achieved by cross-correlation of the time-dependent photothermal signal data with a chirped waveform that is synthesized according to the chirp signal that is used to generate the chirped train of optical pulses from the laser 100.

Figure 2A:
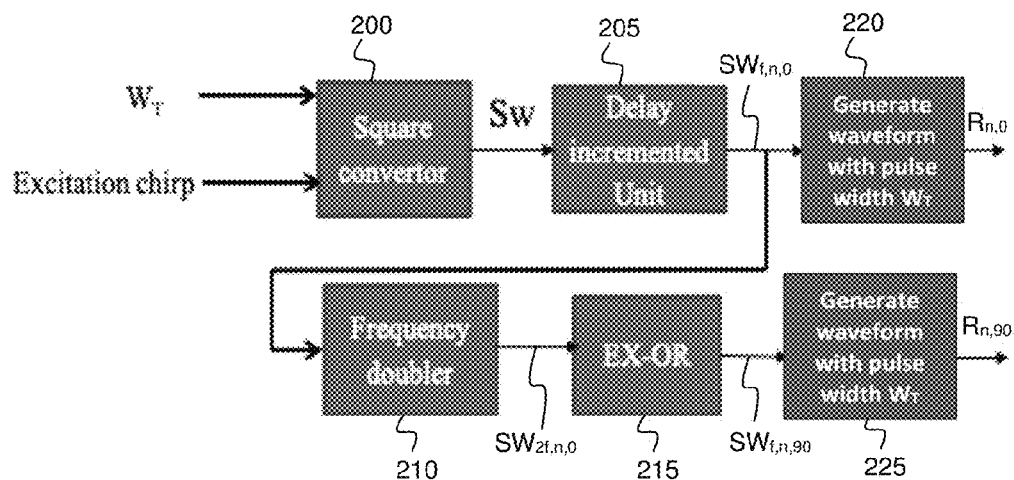
FIGS. 2A and 2B provide block diagrams of an example system for performing enhanced truncation-correlation photothermal coherence tomography.
Figure 2B:
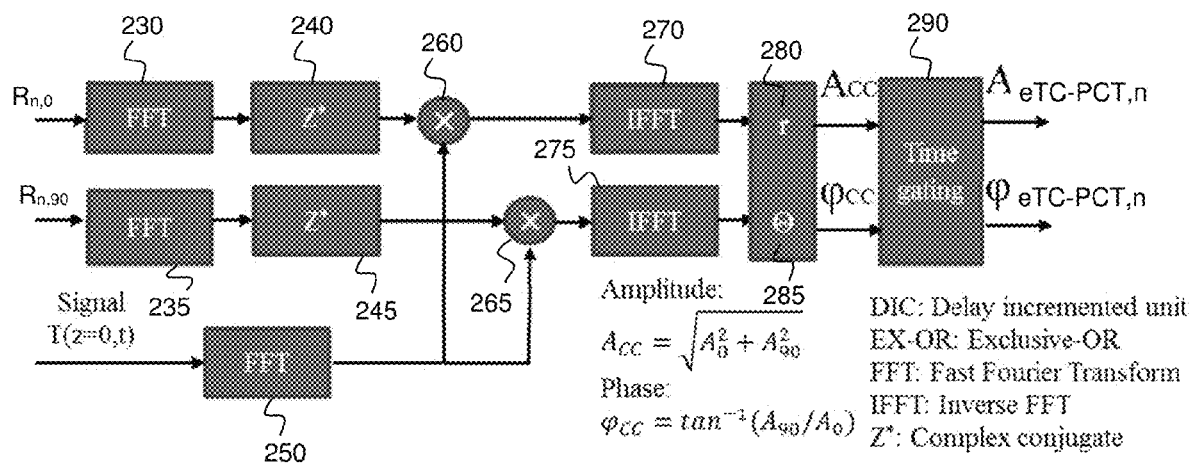

FIGS. 2A and 2B illustrate an example method for performing post-processing according to the eTC-PCT method, involving the use of cross-correlation radar, in which the thermal relaxation chirp is cross-correlated with a set of delayed copies of a reference chirped pulse, with subsequent time gating after cross-correlation. As shown in the figure, the recorded excitation chirp is first converted to a square wave chirp ($S_W$) at 200, and then passed through the delay-sweep module at 205, thereby generating a delay-incremented square chirped waveform ($SW_{f,n,0}$), where n=1, 2, . . . , p counts the slice numbers for which different discrete delays are applied to the respective p waveforms that are generated (with no delay being applied to the first slice). The delay-incremented square wave chirp ($SW_{f,n,0}$) is then frequency-doubled ($SW_{2f,n,0}$) at 210. Subsequently, $SW_{2f,0}$ is subjected to the binary exclusive-or (EX-OR) operation at 215 to generate a quadrature square chirp $SW_{f,n,90}$.

Referring again to FIG. 2A, a step is shown in which pulsed reference chirped waveforms $R_{n,0}$ and $R_{n,90}$ are generated from $SW_{f,0}$ and $SW_{f,90}$, respectively, as shown at 220 and 225, such that each pulse starts at the rising edge of the square signals in $SW_{f,n,0}$ and $SW_{2f,n,0}$ chirped waveforms and has a prescribed pulse width of $W_T$. Unlike the TC-PCT method disclosed in U.S. Pat. No. 9,810,650, which required the generation of truncated reference waveforms with respective truncated pulse widths satisfying $W_T < W_E$ (where $W_E$ is the optical pulse width), in the present example eTC-PCT method, the pulse width of the pulses in the reference chirped waveforms is not limited to being less than the pulse width of the optical pulses. Accordingly, in one example implementation, the reference chirped waveforms $R_{n,0}$ and $R_{n,90}$ may be generated such that $W_T = W_E$, and $W_T < W_E$ or $W_T > W_E$. Since the present method does not require truncation of the excitation chirp, with the option of generating, prior to cross-correlation, a reference chirped waveform with pulse widths satisfying $W_T \geq W_E$, the pre-cross-correlation processing of the reference chirp, as per the eTC-PCT methods disclosed herein, may be referred to as "reference chirped pulse width modification", as opposed to truncation.

As described in further detail below, the axial resolution of eTC-PCT images generated according to the present example methods depends on the pulse width $W_T$ of the reference chirped waveforms. The minimum value for $W_T$ is limited by the camera frame rate, and the maximum is limited by the time difference between the last two pulses/the shortest thermal transient in the chirped waveform. Selecting a large pulse-width/slice-width ratio leads to a lower axial resolution, while it localizes more energy within the slice thickness, thus leading to higher SNR.

According to the workflow illustrated in FIGS. 2A and 2B, multiple reference chirped waveforms are synthesized, with a variable delay/initial-phase (in the present example embodiment, the delay generated according to nd, where n is the slice number (n=0, 1, 2, . . . , p), and where d is the delay step). These reference chirped waveforms are referred to as $R_{n,0}$ and $R_{n,90}$, for the in-phase and quadrature reference chirped waveforms, respectively, where $R_{0,0}$ and $R_{0,90}$ are the initial waveforms with zero delay, and $R_{n,0}$ and $R_{n,90}$ are the nth delayed waveforms that generates the slice number n.

Figure 2C:
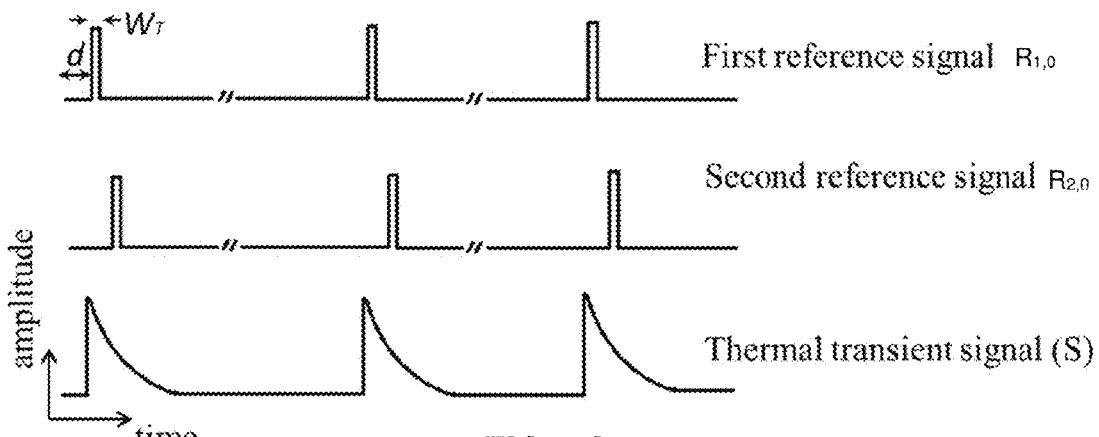
FIG. 2C schematically illustrates different time-delayed reference waveforms and an example transient photothermal response signal.

FIG. 2C schematically illustrates the relationship between the decaying time-dependent photothermal signal S that is detected by the infrared imaging camera, and two example in-phase reference chirped waveforms, $R_{1,0}$ and $R_{2,0}$ that each have a different respective delay, and pulse widths of $W_T$.

Figure 3:
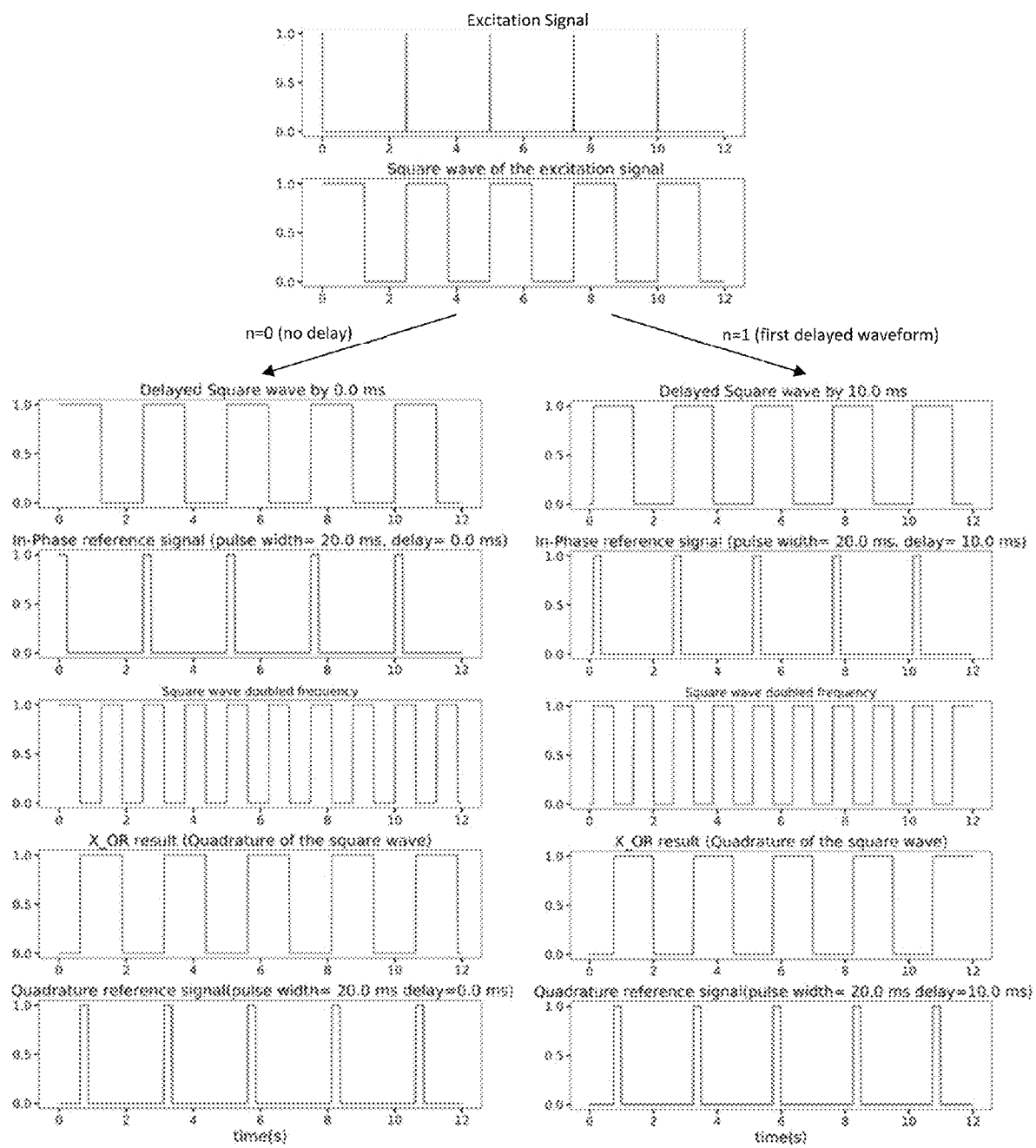
FIG. 3 illustrates various example waveforms generated according to different steps of the block diagrams of FIGS. 2A and 2B.

FIGS. 3A and 3B illustrate example waveforms that are generated according to the example method shown in FIG. 2A. The figure shows the initial excitation waveform (excitation signal) and its square wave counterpart, followed by the generation of the in-phase and quadrature reference chirped waveforms for the example cases of no delay (n=0) and the first delay (n=1). This process is repeated for each delay in order to generate the respective waveforms that facilitate depth-slice processing.

Referring again to FIGS. 2A and 2B, a Fourier transform is then obtained for each of the reference chirps, as shown at 230 and 235, respectively, and the complex conjugate of each transformed reference is calculated, as shown at 240 and 245. A cross-correlation is then performed in the frequency domain whereby the complex conjugate of Fourier transformed reference chirped waveforms, both in-phase and quadrature, is then multiplied with the Fourier transform of the time-dependent photothermal signal (obtained at 250), as shown at 260 and 265. In this step, each reference chirped waveform, having a respective fixed delay time, is cross-correlated with the photothermal signal captured by infrared camera 100, thereby employing radar pulse compression to produce two-dimensional, axially resolved, layer-by-layer images of the sample.

For example, cross-correlation of the initial reference chirped waveforms $R_{0,0}$ and $R_{0,90}$ which are delayed from the laser chirped pulse waveform by a delay nd=0×d=0, with the time-dependent photothermal signal (S, shown for a given pixel), will generate a surface image of the sample when a plurality of pixels are processed. In the case of $R_{1,0}$ and $R_{1,90}$ the resulting image will be that of a near-surface (subsurface) thin layer. As the delay increases, the depth of the layer below the surface also increases. It will be understood that the depth resolution or "thinness" of a correlation image layer will increase as the pulse width $W_T$ of the reference signal shortens. Parameters controlling the maximum penetration depth include the starting LFM frequency, and the period/length of the chirp. For a given chirp and pulse width $W_T$, the depth range is controlled by the chirp repetition period.

Figure 4:
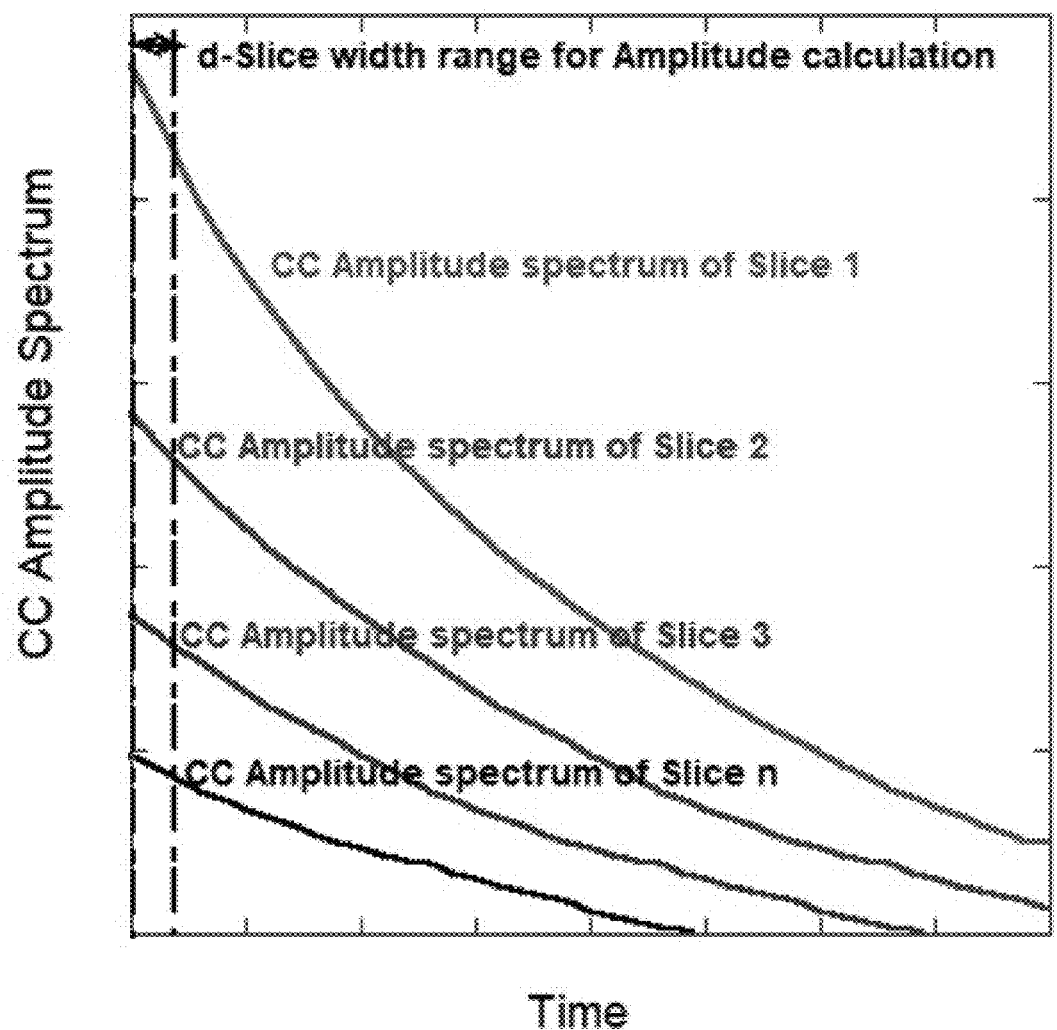
FIG. 4 plots examples of the cross-correlation (CC) amplitude time series of local slices (i=1, 2, . . . , n).

The products are inverse-Fourier transformed, as shown at 270 and 275, to generate the in-phase and quadrature eTC-PCT cross-correlation output, respectively. It is noted that there are two output cross-correlated signal channels, namely $A_0$ and $A_{90}$. These can be construed to be the equivalent of in-phase and quadrature data in polar coordinates, and they can be recast as amplitude and phase, $A_{CC}$ and $\varphi_{CC}$, as shown at 280 and 285. FIG. 4 illustrates example cross correlation (CC) amplitude time series of local slices (i=1, 2, . . . , n), for a given selected slice delay.

Figure 13A:
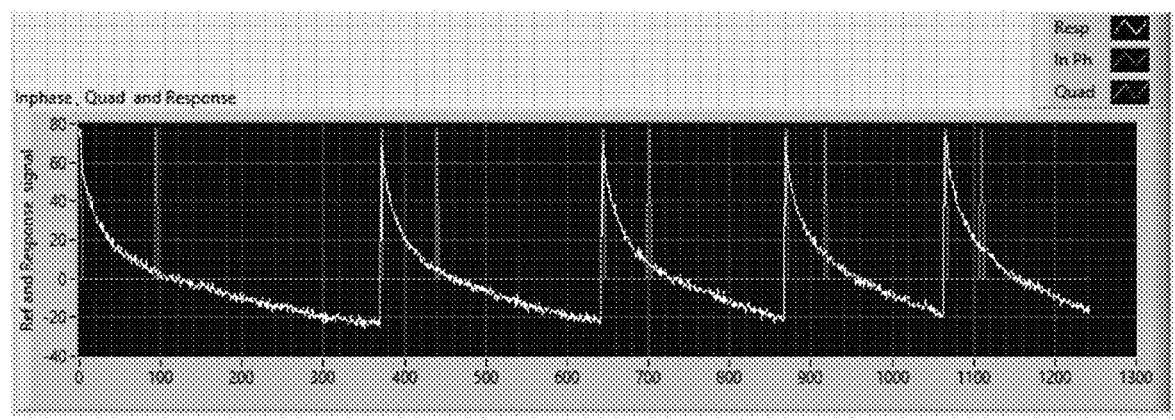
FIG. 13A plots a response signal (white), in-phase (red) and quadrature (green) of the eTC-PCT reference signals that generate the first slice of a 3D eTC-PCT image dataset. This up-chirp signal includes 5 pulses, the first pulse being the longest duration, and the last being the shortest duration.
Figure 13B:
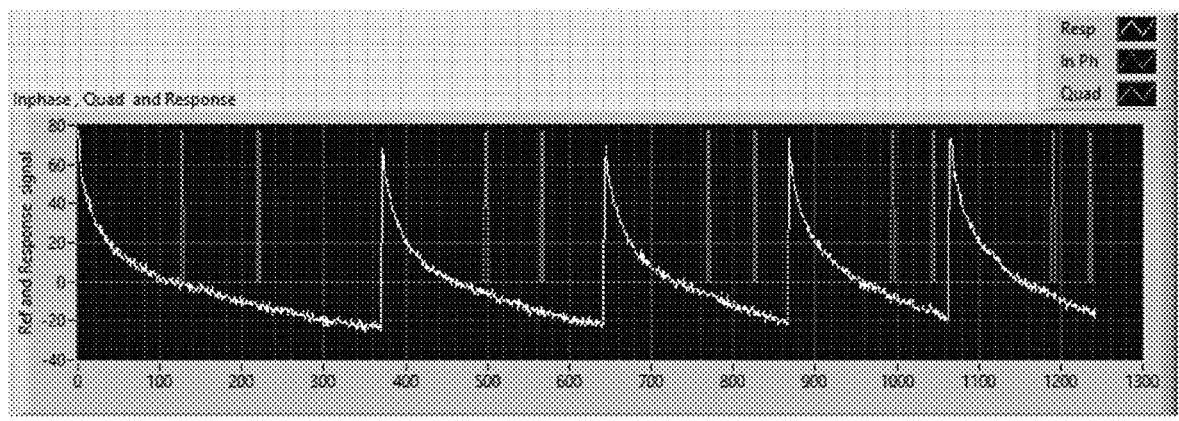
FIG. 13B plots the response signal (white), in-phase (red) and quadrature (green) of the eTC-PCT reference signals that generates the last 3D eTC-PCT slice. The number of slices available in eTC-PCT is determined based on the duration of the last (shortest) thermal transient. Upon cross-correlating the thermal transient with the quadrature reference signal (in green), the fourth pulse should not cross the starting point of the 5th thermal transient signal (white), which is the last and the shortest pulse in the up-chirp train.

As shown in FIG. 2B, the cross-correlation amplitude and cross-correlation phase time series, for each local slice n, is truncated via a time-gating (time windowing) operation shown at 290. The time duration of the time gating is dependent on the delay associated with a given slice. The time duration of the time gating window decreases as the delay associated with the slice increases. The truncation is performed over a time duration that is determined according to a condition that prevents the time-delayed quadrature reference signal of the last excitation pulse from being shifted beyond the excitation chirp time. As shown in FIGS. 13A and 13B, the quadrature reference signal in green should not pass the last pulse of the thermal transient. Therefore, the duration of the shortest thermal transient (Thermal$_{T_D}$) is a criteria to specify the time gating width for each slice.

$$\text{Time gating width} = \text{Thermal}_{T_D} - n \times d$$

wherein n*d is the delay applied to each slice (such that the first slice does not have a delay, n=0, 1, . . . , p), and Thermal$_{T_D}$ is the duration of the last thermal transient (shortest thermal transient in an up-chirp signal).

In other words, according to the present example eTC-PCT method, the time gating truncation duration is based on the maximum achievable range of the Quadrature reference signal of the last excitation pulse in cross-correlation amplitude and phase time series for all slices.

This method lies in contrast to the conventional TC-PCT method that was absent of post-cross-correlation truncation, and in which a full time series was used for each local slice to determine the output images. As a consequence of the use of the full time series for image generation, some TC-PCT images did not match with the location of local absorbers that were hidden below the surface layers.

The present eTC-PCT method thereby employs post-cross-correlation truncation of the resulting cross-correlated signals, in stark contrast to the previously disclosed TC-PCT method. While the TC-PCT method only involved pre-cross-correlation truncation of only the reference chirp waveform, the present example eTC-PCT methods employ post-cross-correlation truncation of a signal that is generated based on both the reference chirped waveform and the detected thermal signal.

The truncation (time gating) of the resulting cross-correlation signals (e.g. the phase and amplitude) facilitates improved depth resolved eTC-PCT amplitude, amplitude delay, phase and phase delay outputs, when compared to the TC-PCT method disclosed in U.S. Pat. No. 9,810,650.

According to the present eTC-PCT method that employs post-cross-correlation truncation, the image data that is employed for generating images of each slice is only selected within the range of time gating width. This aspect has been found by the present inventors to be beneficial in facilitating high resolution 3D imaging of biomedical samples from the detected phase delay time.

When performing the previously disclosed TC-PCT method, amplitude, phase, amplitude delay and phase delay values were calculated for each slice from the full time series of the cross-correlation amplitude and phase time series. As a consequence, the TC-PCT depth order became gradually uncontrollable in deep subsurface region slices, and deep layer images exhibited sudden and unpredictable repetitions of near surface features.

Figure 5A:
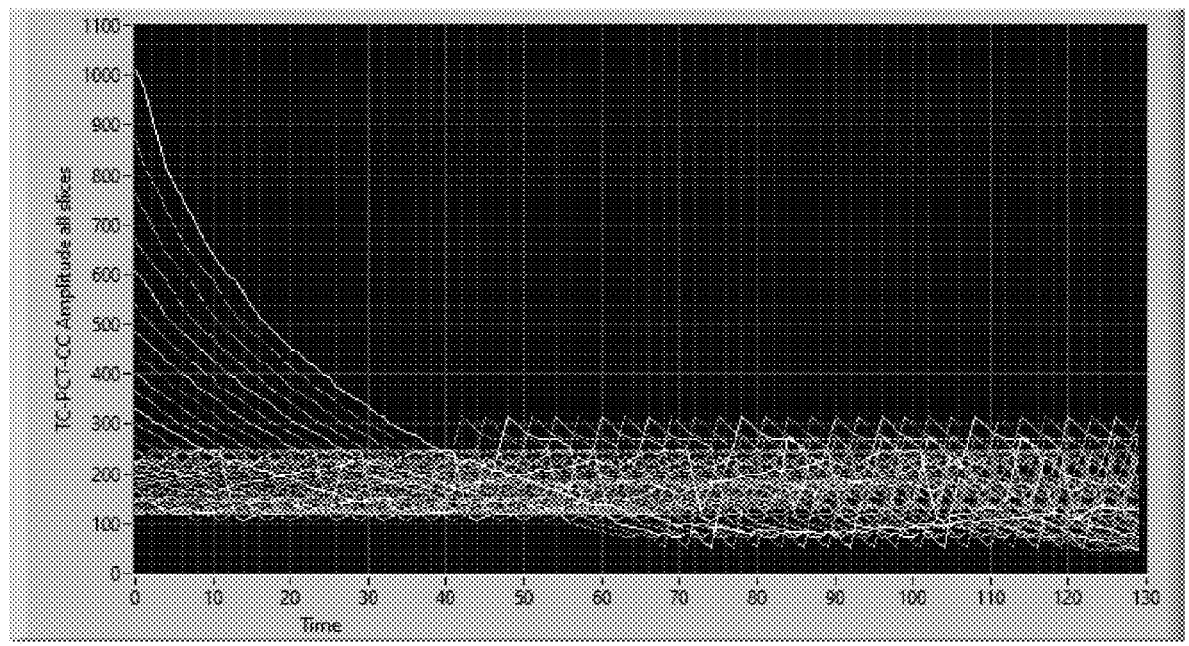
FIGS. 5A and 5B plot example cross-correlation amplitude time slices for (A) the TC-PCT method and (B) the eTC-PCT method.

As example of this susceptibly to depth errors when employing the TC-PCT method is shown in FIG. 5A. For all cross-correlation amplitude slices computed using the TC-PCT method, truncation occurs for each slice in the cross-correlation amplitude time series (transient). The method works reasonably well for calculating TC-PCT amplitudes if the signal-to-noise ratio (SNR) is very high, as shown in the cross-correlation amplitudes of the first 10 slices, so according to the original TC-PCT algorithm, index 0 is the maximum point of each amplitude transient. However, the cross-correlation amplitude transient m of the 3rd slice (bright green) shows that after time-point #40 on the x-axis, the amplitude rises. This rise in amplitude is not a result of the sample properties—rather this is where a second pulse overlays on the thermal transient as a result of cross-correlation.

Figure 5B:
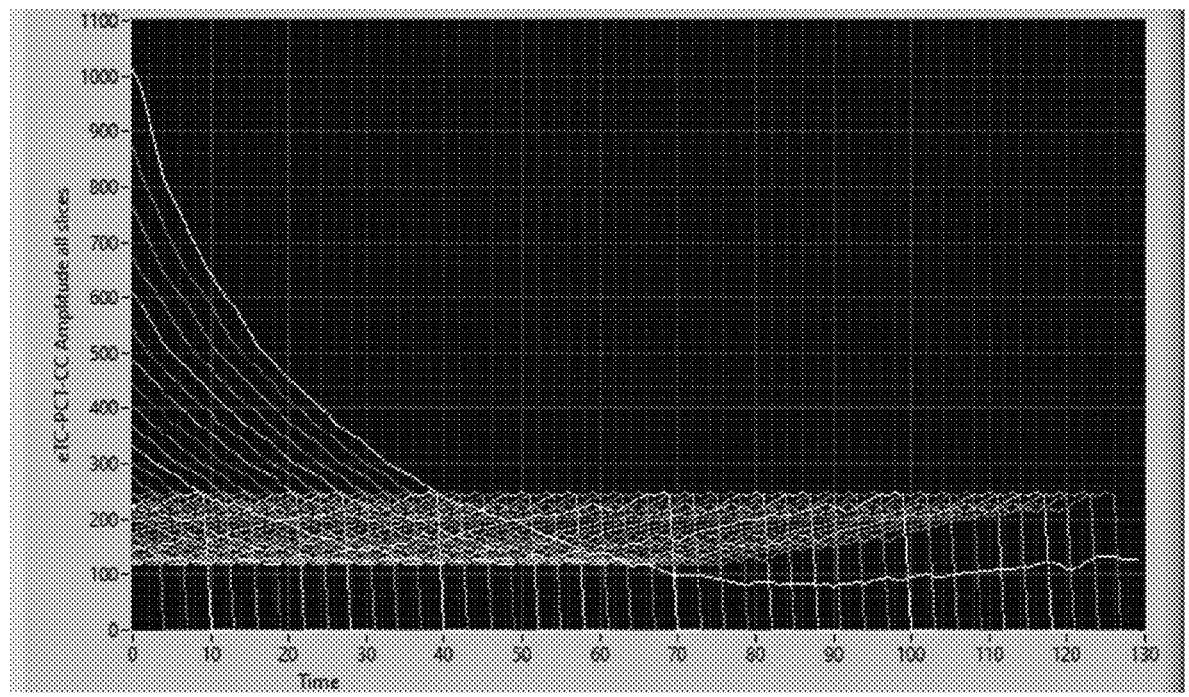

In order to avoid this artefact, the post-cross-correlation temporal truncation of the present eTC-PCT method cuts off the cross-correlation amplitude after the 40th time-point, as shown in FIG. 5B. This plot shows all cross-correlation amplitude time slices computed using the eTC-PCT algorithm. Truncation occurs here for each slice in cross-correlation amplitude time. As shown in FIG. 5B, the 1$^{st}$ slice (white curve), the cross-correlation amplitude transient includes up to 127 (130–3) time points. However, the $3^{rd}$ slice of the cross-correlation amplitude time series (same bright green as before) was cut off 124 (130–3×2) time points. The 11th slice ($2^{nd}$ white curve) of the cross-correlation amplitude was cut off after 100 (130–10×3) time points.

The post-cross-correlation truncation illustrated in FIG. 5B facilitates the ability to represent deep absorbers in regions with lower SNR responses in 3D images. While the present inventors had attempted to avoid this error when performing the TC-PCT method by avoiding the use of local time slices longer than laser-ON times, depth resolved 3D images from deeper regions with weaker SNR could not be obtained with the original TC-PCT algorithm. This problem associated with this limitation of the TC-PCT method is thus avoided in the present eTC-PCT method. Indeed, with ns range lasers used in FIG. 1, local time slices (ms) will be longer than laser ON time (ns) and signal-to-noise ratios will be higher. Hence, the eTC-PCT method, when employed using ns laser sources, can help improve the axial resolution amd image quality of deeply seated absorbers.

An amplitude image may be formed by determining, for each pixel, and for a given delay (i.e. at a given depth), the value of the peak amplitude in the time-dependent amplitude. The resulting two-dimensional set of amplitude values, associated with a given delay (i.e. depth), represents a depth-resolved image. Furthermore, the time locus associated with the amplitude peak may be employed to generate a depth-resolved amplitude delay images.

In one example implementation of the present eTC-PCT method, the phase may also be extracted from the cross-correlation phase time series at the same time value as the amplitude delay. A phase image may be generated by determining, for each pixel, and for a given delay (i.e. at a given depth), the phase value that corresponds to the amplitude peak. It will also be understood that many other different types of images may be obtained by processing the output of the cross-correlation.

In one example implementation, the phase delay time may be determined from the cross-correlation phase time series at a point on the time axis where the local phase changes sign (negative to positive or vice versa). The phase delay output of that local slice is this time value.

The present example eTC-PCT methods can be beneficial in providing several potential benefits relative to the TC-PCT method. For example, according to one example implementation of the eTC-PCT method, the number of local slices available to improve the axial resolution of the 3D structures depends only on well-defined user selected parameters of the excitation chirp signal. Control methods of this number were not disclosed in the original TC-PCT method.

Furthermore, according to the eTC-PCT method, the phase is extracted from cross-correlation phase time series at the same time axis index as the amplitude delay, which can facilitate high resolution phase outputs at each local slice. In contrast, the TC-PCT method prescribed that the phase was computed over all points in the cross-correlation phase time series of each slice. As a result, phase images were not reliable for biomedical samples with low SNR.

Also, according to the TC-PCT method, the number of local slices available to improve the axial resolution of 3D structures was limited to laser-ON time of the excitation signal, which need not be a constraint in the present example eTC-PCT method. Since eTC-PCT method employs truncation after cross-correlation, there is no need to truncate the laser-ON time (optical pulse width) of the chirp excitation signal. The laser-ON time range (ms) is only required to determine the energy needed to generate thermal responses from the probing region. This condition may be removed when performing the present eTC-PCT, thus facilitating the use of ns-duration pulsed laser image generation and depth-resolved quantitative 3D imaging even with ns range laser pulses and thermal responses up to several seconds.

Furthermore, when performing the TC-PCT method, the output of each local slice was only selected at the maximum value of the cross-correlation amplitude time series. While this may be acceptable for reconstructing 3D images based on a single absorber in the detection rage of the probing depth, problems may arise in generating true 3D reconstructions of multiple absorbers hidden within the probing depth. This limitation may be removed when performing multi-wavelength eTC-PCT, thus improving the sensitivity to multiple absorbers within the probing depth.

In some example implementations, depth resolved (according to each local slice) outputs may be generated according to (or based on) any one or more of phase delay, phase, amplitude and amplitude delay, and optionally employed to generate 3D thermophotonic images. A sequence of 2D truncated-correlation amplitude images at increasing depths below the surface can be generated by incrementing the value of delay/initial-phase.

As noted above, the repetition time of the chirp defines the maximum depth probed, form which thermal information arrives at the surface. This is due to the thermal conduction time $t \sim Cx^2/\alpha$, where x is the depth probed, and a is the thermal diffusivity of the material, and C is a factor close to unity. In the above equation, x would be the only depth involved in conventional lock-in thermography. In the example eTC-PCT methods disclosed herein, however, depth is controlled by the initial time gate that is applied pre-cross-correlation, opened at a fixed delay, as prescribed by the delay values of the various reference waveforms that are employed for cross-correlation. This use of time-gated reference waveforms at different delays (and therefore different depths) gives rise to sequences of image sheets which comprise the 3D volume of the image when stacked up.

In some example implementations, depth coded two-dimensional amplitude/Phase images may be stacked to form the three-dimensional eTC-PCT amplitude tomograms.

As noted above, each reference chirped waveform can be cross-correlated with the time-dependent photothermal signal data captured by the infrared camera, in a pixel-by-pixel manner, in order to produce two-dimensional, axially resolved, layer-by-layer images of the sample. For example, cross-correlation of the reference, which is in phase with excitation chirp, with the PT image chirp, will give a surface picture of the sample. As delay/initial-phase increases, the depth of the layer below the surface also increases. Furthermore, the depth resolution (thinness of an image layer) will increase as $W_T$ shortens. The eTC-PCT is thus analogous to a bandpass filter whose operating frequency and quality (Q) factor are variable.

The time-dependent photothermal signal data (PT relaxation signal, following a pulsed excitation, is continuous in the frequency domain and during eTC-PCT execution the frequency contributing the planar image keeps on decreasing with the increase in delay/initial-phase. Parameters controlling the maximum penetration depth are the starting LFM frequency and period/length of the chirp.

In some embodiments, a single reference chirped waveform may be generated in order to obtain photothermal image data at a single depth within the sample. In other embodiments, two or more reference chirped waveforms may be generated. As described below, the generation of multiple images at different depths may be employed to generate volumetric image data. For example, by incrementing the initial phase/delay of the split-reference chirp and sampling the radar output at a fixed position, one can obtain a sequence of time-coded data that yields a depth coded photothermal profile of the medium.

The image data can also be employed to generate time-dependent, depth-resolved images based on the photothermal data. For example, using an infrared camera, the evolution of surface temperature can be recorded and the output can be translated to a sequence of frames of two-dimensional depth-coded images with a high degree of localization. These images can be stacked to produce a volume visualization of photothermal properties of the sample. This swept-correlation process in the time domain is analogous to a continuously tunable band pass filter in the frequency domain.

While the operating/central frequency of the system is controlled by the delay of the chirped-pulse with respect to the excitation pulse, the pass-bandwidth or quality factor is determined by the pulse width of the reference chirp. In cross-correlation thermal-diffusion-wave fields, the delay controls the time gating of the cross-correlation depth while the pulse width of the reference chirp determines the degree of energy localization (axial resolution).

It is noted that in contrast to time-domain thermal relaxation signals that lack phase, the images that are generated according to the present eTC-PCT methods can provide amplitude, time-delay and phase for the matched filter, all of which can carry depth resolved energy localization information with more or less sensitivity and dynamic range. As noted above, the axial resolution is determined based on the pulse duration of the reference chirp—i.e. the shorter the pulse duration, the greater the axial resolution will be due to the improvement in energy localization. Irrespective of pulse width, the delay-sweep increment determines the depth sampling interval.

It will be understood that depth-resolved image data can be obtained provided that the pulse width of the reference chirp is less than the thermal relaxation time of the material being measured. This implies that if a given time-gated pulse chirp were replaced by an expanded pulse chirp, such that the pulse duration became comparable with the thermal relaxation time, then a depth integrated, rather than depth resolved, thermal-wave picture of the sample will emerge through the radar channels. In such a case, the features of regular lock-in thermography would be obtained.

The enhanced truncated-correlation photothermal coherence tomography (eTC-PCT) method described above is believed, by the inventors, to provide the highest energy localization modality in a parabolic diffusion wave field to-date. As noted above, eTC-PCT uses a cross-correlated pulse-chirped radar approach in which broadband thermal relaxation is cross-correlated with a delay-swept reference chirped waveform. The pulse width of the reference chirp determines the depth (axial) resolution while the delay with respect to the excitation chirp controls the depth range by controlling the time-gating width. Both parameters may be operator selectable. It has been found that among the available outputs (amplitude, initial phase, peak delay time, and zero-phase delay), the mixing of the amplitude and the phase offers the highest dynamic range and sensitivity. This feature has been verified both theoretically and experimentally, as shown in the examples provided herein. Furthermore, by stacking depth-scaled planar images generated through phase incrementing the truncated coherent reference, eTC-PCT can create three-dimensional visualizations of the distribution of optothermal parameters of the target similar to optical coherence tomography (OCT) but with considerably higher depth range (millimeters instead of submillimeter).

As described above, the depth-resolved images may be prepared according to a wide variety of parameters, including amplitude, phase, and delay. The depth resolved images may be further processed according to a wide variety of image processing algorithms in order to obtain different renderings of the image data. For example, when multiple depth-resolved images are combined to obtain volumetric image data, the volumetric image data may be processed according to a binarized thresholding algorithm in order to render the volumetric image data in a binarized format for display.

Figure 6A:
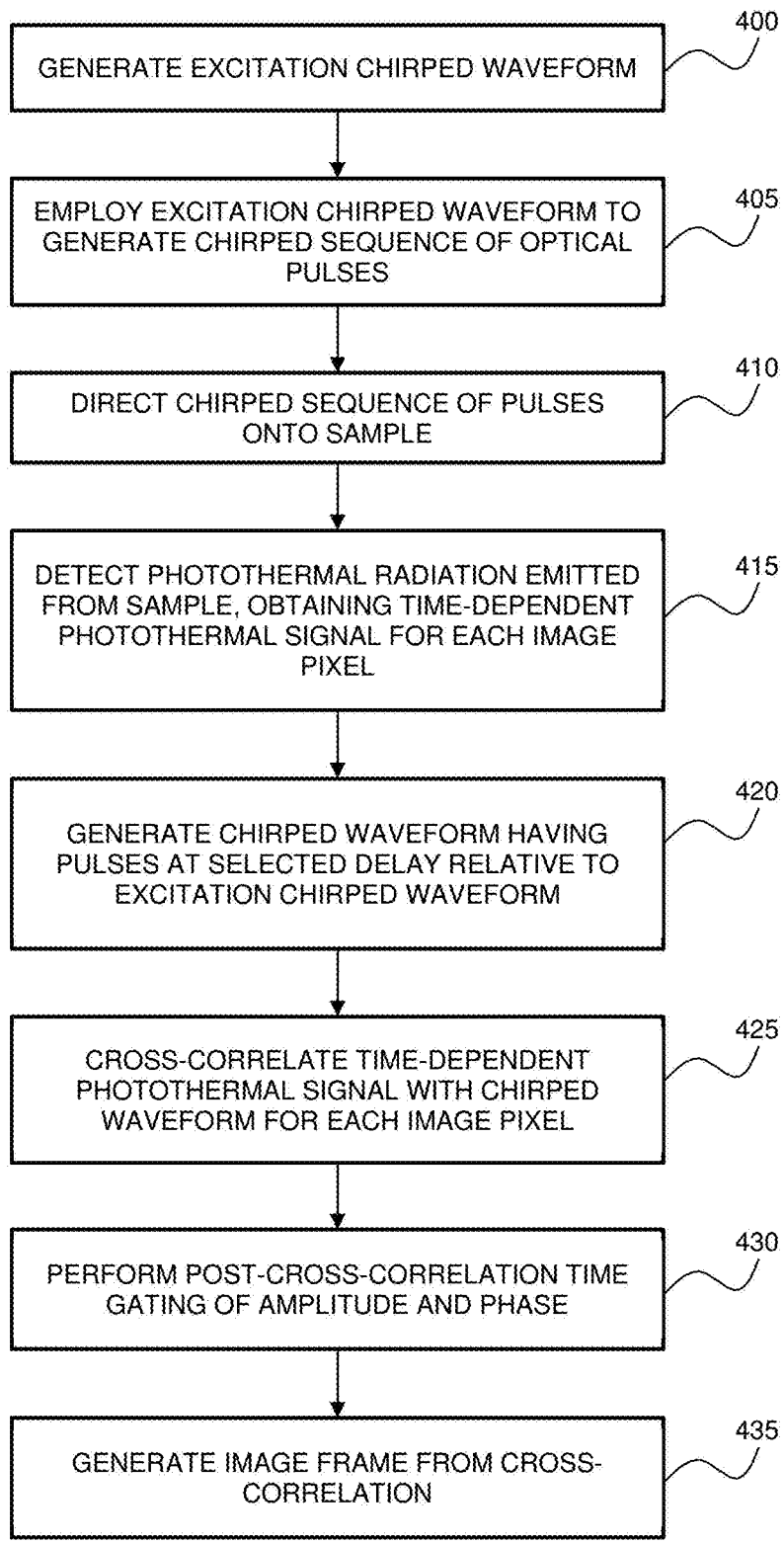
FIG. 6A is a flow chart illustrating an example implementation of truncated-correlation photothermal coherence tomography.

The preceding workflow is summarized in the flow chart illustrated in FIG. 6A. In step 400, an excitation chirped waveform is generated. The excitation chirped waveform may take the form of a set of fixed width pulses having a chirped repetition rate, as described in the preceding examples. It will be understood that other chirped pulse profiles may alternatively be employed. The resulting chirped sequence of pulses is then delivered onto the sample at step 410, and the resultant photothermal radiation is detected by the infrared imaging camera at step 415. The camera detects multiple image frames, such that a time dependent signal is obtained for each pixel of the camera.

The time-dependent photothermal signal obtained from each pixel is then processed according to the eTC-PCT method, as shown in steps 420 and 425. At least one chirped waveform is generated at step 420, when each chirped waveform is may be processed to generate a reference chirped waveform having a pulse width that is optionally be less than, equal to, or greater than, the excitation pulse width, for a given delay. Each pulse in the reference chirped waveform is delayed by a pre-selected time delay relative to a corresponding pulse of the initial excitation chirped sequence of pulses.

Each reference chirped waveform is then cross-correlated with the time-dependent photothermal signal for each pixel in step 425. This may be performed, for example, using the methods described above involving in-phase and quadrature multiplication in the frequency domain. After performing cross-correlation, the time-dependent amplitude and phase profiles are subjected to time gating, as shown at 430. The resulting cross-correlated and time-gated data, obtained for each pixel and for each reference chirped waveform (i.e. for each delay), is then employed to generate one or more depth-resolved images, as shown in step 435.

Figure 6B:
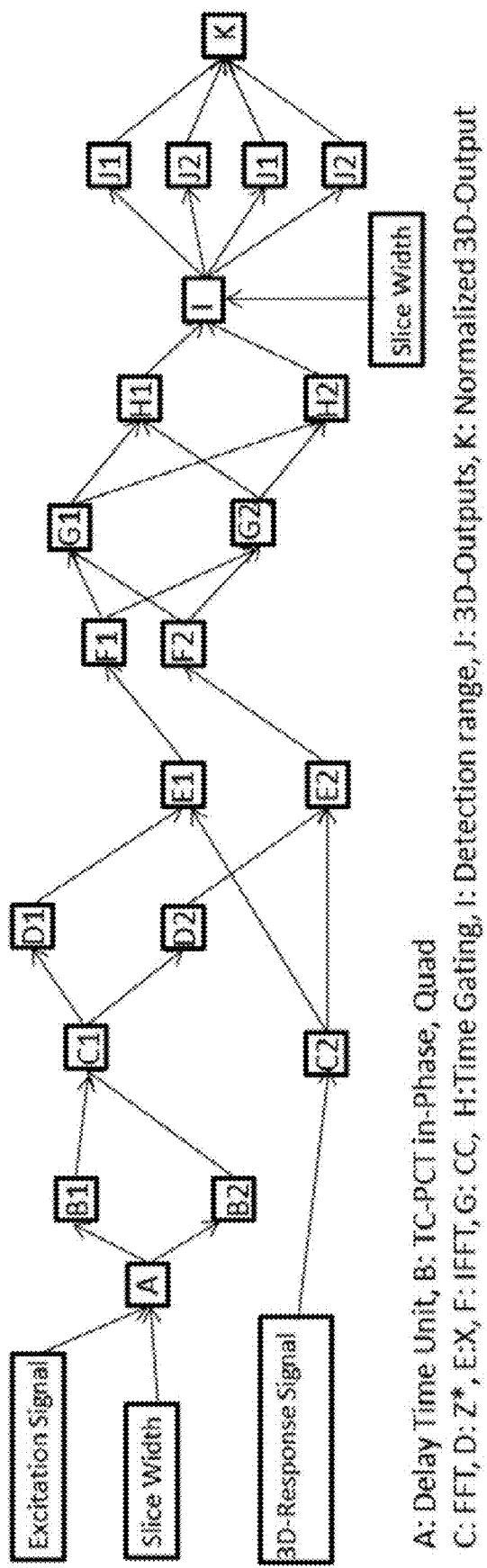
FIG. 6B schematically illustrates and example deep learning algorithm for eTC-PCT imaging.

FIG. 6B illustrates an example method for training a deep learning (DL) algorithm to speed up the signal processing of eTC-PCT to generate high resolution 3D images. The present inventors have found that the preceding example method of pixel-by-pixel eTC-PCT data outputs for 3D imaging can require up to a few hours to generate maximum achievable spatial and axial resolution of the 3D images. By implementing deep learning algorithms to process eTC-PCT data with maximum achievable spatial and axial input parameters, signal processing time and computer memory limitations are optimized to provide depth resolved 3D output images within a few minutes for clinical applications.

Theoretical Model of eTC-PCT

The excitation signal which is a linear frequency modulated pulse chirp is represented in Eq. 1

$$E(t) = \sum_{m=0}^{P} \delta\left[t - \left(\frac{-\omega_1 + \sqrt{\omega_1^2 + 2\pi r(4m+1)}}{2r}\right)\right] \quad (1)$$

Where $\omega_1$ is the staring angular frequency and $r=(\omega_2-\omega_1)/T$ is the sweep range with $\omega_2$ being the ending frequency and T being the signal period.

The in-phase ($R_{0,n}$) and quadrature signals ($R_{90,n}$) reference signals are synthesized from the excitation signal, E(t). The procedure of generating in-phase and quadrature signals is elaborated in FIG. 2A and FIG. 3. The present example technique cross-correlates the in-phase and the quadrature of the reference chirp with the photothermal images (S) captured by the camera in a pixel-by-pixel format:

$$CC_{n;0/90}(t) = \int_{-\infty}^{\infty} R_{n;0/90}^{*}(t+\tau) T_{chirp-pulse}(\tau) d\tau \quad (2)$$

S stands for the thermal transient in each sub-period and is defined pictorially in FIG. 2C.

For fast calculations, the cross-correlation is executed in the frequency domain.

Finally, the cross-correlation amplitude and phase can be calculated from $$A_{CC,n} = \sqrt{CC_{n,0}^2 + CC_{n,90}^2} \quad (3)$$

and $$\emptyset = \tan^{-1}(CC_{n,90}/CC_{n,0}). \quad (4)$$

In some example implementations, the amplitude peak value is measured from the cross-correlation amplitude, Eq. (3). From the cross-correlation phase, Eq. (4), the phase value at the amplitude peak time provides the phase of one pixel. The present example method, however, searches for the amplitude peak within a truncated, gated time window based on the distance between the last two consecutive pulses in the full duration of the excitation signal waveform, and is based on the following formula for the applied delay to the reference signals:

$$\text{Time gating width} = \text{Thermal}_{TD} - n \times d \quad (5)$$

wherein n×d is the delay applied to each slice (such that the first slice does not have a delay, n=0, 1, . . . , p), and Thermal$_{T_D}$ is the duration of the last thermal transient (shortest thermal transient in an up-chirp signal).

From the resulting cross-correlation amplitude, the value and the time corresponding to the peak amplitude of the cross-correlation produces the amplitude and amplitude delay information, respectively. From the resulting cross-correlation phase, the phase value at peak amplitude and time corresponding to zero phase value may be employed to provide the phase and phase delay data for one pixel, respectively. The time corresponding to zero phase value specifies the net thermal flux of zero. Given that the phase delay channel determines at which point of the time axis the phase trace crosses from negative to positive or vice versa, for biomedical tissue samples and other materials.

Multispectral Imaging

As described above, the preceding example eTC-PCT system and method may be performed in a multi-wavelength or multispectral configuration. For example, as shown in FIG. 1, the output of the pulsed laser source 100 may be fed to an optical parametric oscillator 105, which generates a corresponding wavelength-shifted and wavelength-tunable chirped pulse train. By scanning the wavelength of the incident optical pulses, eTC-PCT data may be obtained at different wavelengths, thereby generating multispectral data and facilitating the generation of multispectral images.

Spatial Gradient Adaptive Filter

In one example embodiment, a spatial-gradient-gate adaptive filter may be applied to image data (e.g. one or more diffusive thermophotonic images, such as those obtained according to the present example eTC-PCT methods) to improve image quality. The present example method has been found to improve the absorber spatial extent shown in a diffusive thermophotonic images and restore pre-diffusion lateral image resolution beyond the Rayleigh criterion limit. The example adaptive filter method has been observed to reduce or minimize the effect of thermal diffusion-wave broadening and signal overlapping along the x and y coordinates of each image slice.

According to one example implementation, an example spatial filter operates in a (x,y) coordinate scanned mode over an image slice (e.g. a slice having given depth). The spatial filter operates as a resonant gate, producing a peak when the spatial width of the gate matches a size of a steepest lateral gradient of signals produced by a finite-size absorbing region in the image. In this manner, (photo) thermal-diffusion-broadened regions beyond absorber edges/boundaries are identified and filtered out, and lateral image resolution is restored approximately to pre-diffusion true absorber sizes, especially at large (>2-mm) depths. This method may improve contrast against background.

In one example embodiment, the spatial-gradient-gate adaptive filter method may be separately applied to the sequence of broadened features along both the x and the y axes, thereby generating two filtered images. The two computed images may then be combined (e.g. averaged) to generate a composite image. In one example implementation, the thermophotonic image resolution restoration filter may be applied to a mixed pulsed eTC-PCT amplitude and phase image. A mixed image may be obtained by multiplying the amplitude and phase results at each pixel, providing details of both channels in one.

Assuming a temporal Dirac delta function (spatially impulsive) absorption line in homogeneous and isotropic space, the one-dimensional temperature field along the x coordinate (x=0 on the surface) can be written as a diffusive function of time (t) and the object's thermal diffusivity ($\alpha$):

$$F(x,t) = \frac{1}{\sqrt{\pi \alpha t}} e^{-x^2/4\alpha t} \quad (7)$$

For simplicity, the time-dependent pre-exponential factor can be ignored or lumped into a constant $A_j \equiv A(t_j) = 1/\sqrt{\pi \alpha t_j}$ for a fixed instant $t=t_j$ at which a camera image is recorded. The spatial gradient-gate adaptive filter consists of two scanning coordinate points $x_1$ and $x_2$ which constitute a moving spatial gate of width $\Delta x = x_2 - x_1$ and are related to each other through a constant c (adjustable, but fixed throughout a given scan) as follows:

$$x_2/x_1 = c \quad (8a)$$

As these spatial points, subject to the constraint (3a), are scanned along each x coordinate (pixel) line within a predetermined (x,y) area of the instantaneous image recorded by the camera, the function $$g(x_1,x_2;t_j)=F(x_1,t_j)-F(x_2,t_j)=A(t_j)(e^{-[x_1/X(t_j)]^2}-e^{-[x_2/X(t_j)]^2}) \quad (8b)$$

where $$X(t_j)=2\sqrt{\alpha t_j}. \quad (8c)$$

is a thermal diffusion length of signals generated following optical absorption and nonradiative energy conversion to a heat source which subsequently diffuses during time $t=t_j$, Eq (7). The function g represents a moving spatial signal contrast gate of width $\Delta x$. If the constant c that determines the fixed distance between $x_1$ and $x_2$:
$x_2-x_1=(c-1)x_1$, and makes g a function of $x_1$ only, is set so that g exhibits a maximum value under the condition $$\frac{dg(x_1,t_j)}{dx_1} = A_j(t_j)\frac{d}{dx_1}\left(e^{-[x_1/X(t_j)]^2} - e^{-c^2[x_1/X(t_j)]^2}\right) = 0, \quad (9)$$

the maximum of g occurs within the scanned spatial gate $\Delta x_{max}=(x_2-x_1)_{max}$ when $x_2$ is related to $x_1$ through the condition Eq. (9) which yields $$X(t_j) = \left[\frac{x_2^2 - x_1^2}{2\ln(x_2/x_1)}\right]^{1/2} \quad (10)$$

Manipulating Eq. (9) and using Eq. (8a) leads to the condition for the appearance of a $g(x_1,t_j)$ maximum when the spatial gate width $\Delta x$ satisfies the relation $$\Delta x = \Delta x_{max} = (c-1)\left(\frac{2\ln c}{c^2-1}\right)^{1/2} X(t_j) \quad (11)$$

This relation shows that if c (and thus $\Delta x$) is chosen appropriately, the gradient of the moving spatial gate $g(x_1,t_j)$, Eq. (11), matches the steepest spatial gradient of the laterally diffusing signal gate, Eq. (3b), when the latter lies within the moving (scanning) spatial gate $\Delta x$. It is well-known that the steepest thermal gradient occurs at the effective edge of an optical absorber acting as a thermal source. The foregoing physical process represents a form of spatial resonance (matching) between the slopes of the decaying diffusive profile $g(x_1,t_j)$ and $\Delta x_{max}$.

In the eTC-PCT images, $g(x,t_j)$ represents the signal difference at the two locations:

$$g(x,t_j)=S(x_1,t_j)-S(x_2,t_j) \quad (12)$$

generated by finite-size absorbing regions in the image. In this manner, thermal-diffusion-broadened boundaries beyond absorber edges, especially at large depths, are identified following steepest decay gradients and filtered out, whence lateral image resolution is approximately restored to true absorber sizes.

Therefore, the position of the $g(x,t_j)$ peak obtained from scanning the $\Delta x_{max}$ gate becomes the criterion for lateral resolution enhancement. In practice, c>1 can be chosen to be small so that $x_1$ and $x_2$ are close when signal gradients are expected to be steep or at early diffusion times, thus enhancing image lateral spatial resolution. c can be chosen to be large when gradients are small or at longer diffusion times, spreading out in space, so that $x_1$ and $x_2$ are relatively farther apart and spatial resolution is expected to be low. The optimal value of c in a given image configuration is obtained ("adapted") for maximum peak value starting the scanning when $g(x_m,t)$ is close to zero and lateral image cut-off is determined by $x_{max}$, the coordinate point $x_1$ at which the $\Delta x_{max}$ maximum occurs. This turns out to be a good approximation. The precise location of the $g(x,t_j)$ maximum can be found from Eqs. (8b) and (10) to be at $$x_{1,max}(t_j) = \left(\frac{2\ln c}{c^2-1}\right)^{1/2} X(t_j) \quad (13)$$

It is noted that the position of the maximum and Eq. (8c) can be used to calculate the thermal diffusivity of the diffusing feature.

Example Applications

It will be understood that the present example methods, and variations thereof, may be adapted and employed for a wide variety of applications. Many studies have shown the potential of utilizing passive infrared imaging temperature measurements as a structured methodology for breast lesion screening, based on a healthy control group to establish expected normality ranges, and abnormal images breast cancer patients previously diagnosed through biopsies of the affected regions. The literature results demonstrated that passive thermography has potential for utilization as a noninvasive screening exam for individuals with breast anomalies, indicating whether the patient should be subjected to a biopsy or not. While active thermography has higher sensitivity, higher resolution and contrast and thus higher specificity compared to passive thermography, it has never been used for breast cancer detection. This is in large part due to the fact that diffusive thermal wave imaging used in active thermography is depth integrated within a thermal diffusion length below the surface. This property tends to hide minute signal differences due to abnormalities like the onset of cancerous growth in the interior.

Of relevance to subsurface cancer diagnosis in humans, in the small animal study described below, eTC-PCT proved the ability to observe the presence of a tumor in the core of the vasculature network in 3D. This method is capable of producing depth-resolved, molecularly specific, subsurface images unlike the temperature contrast-based non-specific conventional thermography. It features deeper penetration than purely optical imaging due to the relative insensitivity to scattering of thermal MIR photons replicating the VIS/NIR absorption profiles of subsurface lesions. Its molecular level contrast is further enhanced by multi-wavelength spectroscopic imaging with wavelength-tunable laser sources, operator controlled higher axial and spatial resolution compared to other diffusion-limited thermal imaging modalities leading to high sensitivity to vascular detection and high speed 2-D/3-D tomographic imaging capabilities (less than 80 s). Since eTC-PCT is non-invasive and involves a relatively simple and inexpensive thermophotonic system, it can be used for preclinical/clinical breast cancer detection, surface tumors (melanomas), dental caries diagnostics, near-surface bone density assessments and endoscopic imaging (TP catheters for coronary atherosclerotic vulnerable plaque and other internal organ imaging).

For example, the eTC-PCT method may be employed for biothermophotonic detection of breast cancer, involving co-registering active multi-wavelength pulsed eTC-PCT and passive thermography images. The passive thermogram provides temperature variation image profiles of the tissue (higher temperature in tumor areas) and surrounding regions and acts as a tumor identifier, whereas pulsed laser-induced multi-wavelength eTC-PCT imaging contributes molecular specificity and high lateral and axial resolution within the tumor area. Known image processing methods may be employed analyze the co-registered breast images to detect the signs of disease, allowing the early detection of breast cancer. In one implementation, a convolutional neural network (CNN) algorithm may be employed for the extraction of the breast characteristic features based on bio-data, image analysis, and image statistics to classify the breast images as normal or with suspected cancerous lesions.

In another example implementation, the eTC-PCT method (and optionally the spatial-gradient-gate adaptive filter method) may be employed to produce images of dental carious lesions, erosion and bacterial demineralization in teeth.

Figure 7:
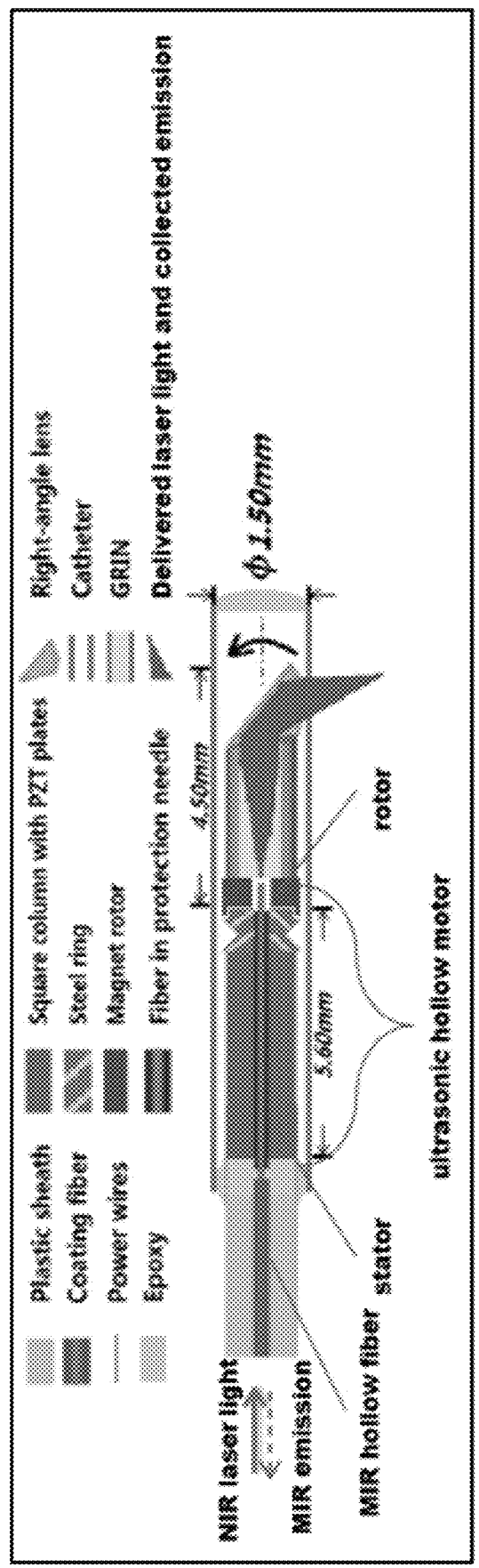
FIG. 7 schematically illustrates an example implementation of an eTC-PCT coronary artery endoscopic catheter.

In another example embodiment, the eTC-PCT systems and methods described above may be adapted to provide a small-size, 3D endoscopic imaging technology with potential advantages over photoacoustic tomography, instrumentally simpler without the need for ultrasonic transducers, using a small fiber-optic diameter (0.25 mm), high contrast, lateral resolution (100 μm) and axial resolution (25 μm). FIG. 7 illustrates a design schematic of an endoscopic catheter, which improves upon an OCT catheter. Comparable or thinner than other current intravascular catheters, the eTC-PCT catheter can conveniently fit inside human coronary arteries (~1 mm dia.)

Figure 8A:
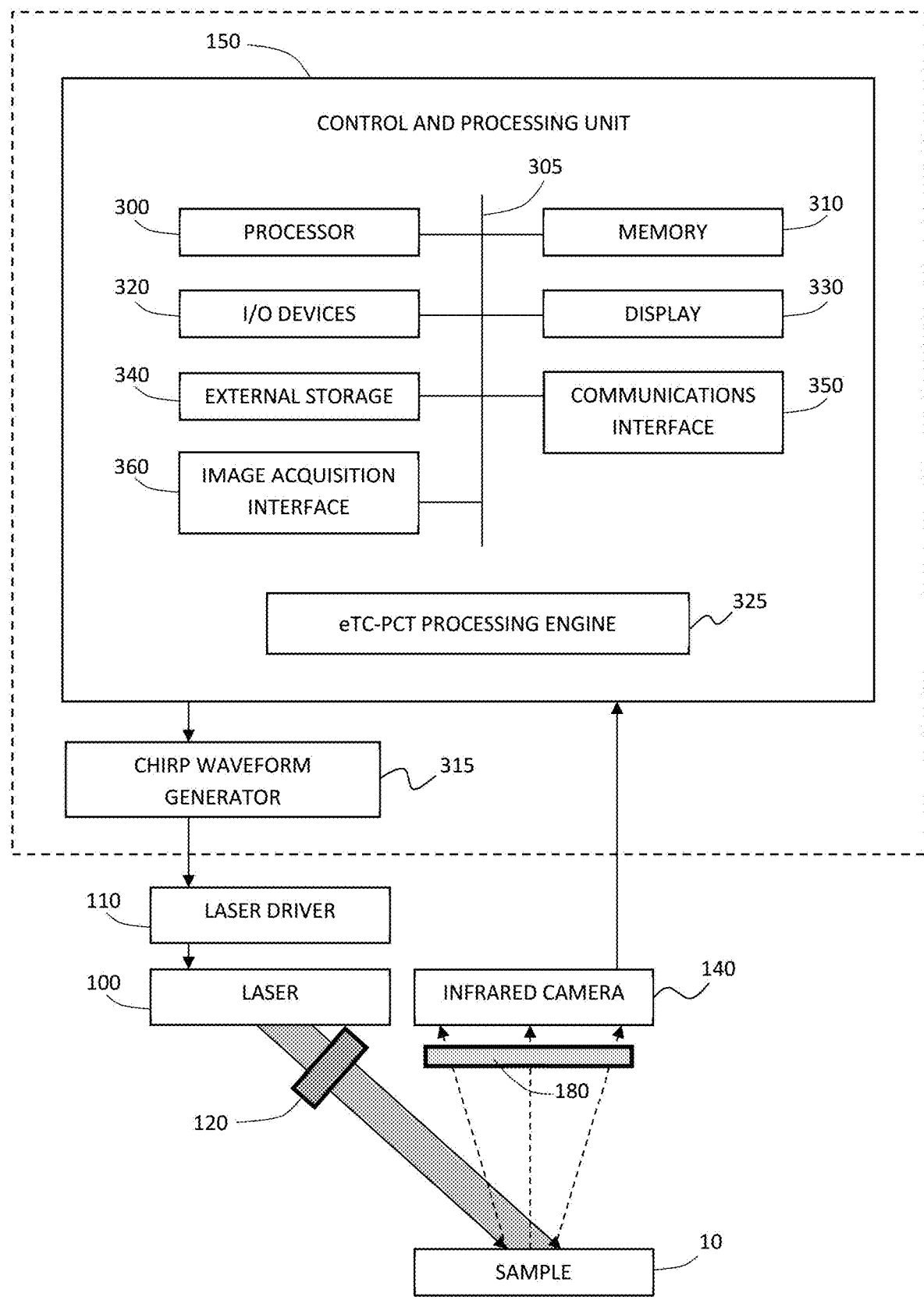
FIGS. 8A-8C schematically illustrates example systems for performing eTC-PCT and related methods.

Referring now to FIG. 8A, another example system is provided for performing eTC-PCT imaging. As in FIG. 1, the system includes a laser 100 (driven by laser driver 110) that directs pulses onto sample 10, where the pulses are delivered in a chirped format, based on a chirped waveform provided by chirp waveform generator 315. Chirped waveform generator 315 may, for example, be configured to generate constant-width pulses with a chirped pulse delay, as illustrated in FIG. 1. Laser 100 may have an integrated laser driver, or a separate laser driver 110. The emitted laser beam may optionally be homogenized by beam homogenizer 120, and additional beam conditioning optics, such as, but not limited to, lenses, filters, mirrors, apertures, beam collimators and/or beam diffusers, may be employed. The emitted photothermal radiation is detected by infrared imaging camera 140, and a filter 180 may be provided to filter extraneous optical radiation incident on infrared imaging camera 140.

Imaging camera 140 is an infrared imaging camera configured to detect photothermal radiation emitted from the sample. As discussed above, a suitable imaging camera is a mid-infrared imaging camera, such as the Cedip 520M.

As shown in FIG. 8A, in one embodiment, control and processing circuitry 150, may include a processor 300, a memory 310, a system bus 305, an image acquisition interface 360 (such as a frame grabber), one or more input/output devices 320, and a plurality of optional additional devices such as communications interface 350, display 330, and external storage 340.

It is to be understood that the example system shown in the figure is not intended to be limited to the components that may be employed in a given implementation. For example, the system may include one or more additional processors.

One or more components of control and processing circuitry 150 may be provided as an external component that is interfaced to a processing device. For example, image acquisition interface 360 may be an external interface, or may reside on a card directly interfaced with a computing device. Furthermore, as shown in the figure, chirp waveform generator 315 may be included as a component of control and processing circuitry 150 (as shown within the dashed line), or may be provided as one or more external devices, as shown in FIG. 10.

Embodiments of the disclosure can be implemented via processor 300 and/or memory 310. For example, the functionalities described below can be partially implemented via hardware logic in processor 300 and partially using the instructions stored in memory 310. Some embodiments are implemented using processor 300 without additional instructions stored in memory 310. Some embodiments are implemented using the instructions stored in memory 305 for execution by one or more general purpose microprocessors. Thus, the disclosure is not limited to a specific configuration of hardware and/or software.

As shown in the figure, the control and processing circuitry 150 includes eTC-PCT processing engine 325, which comprises algorithms for performing the eTC-PCT methods described herein, stored as computer-readable instructions in memory 310 to be executed by processor 300.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

While the preceding example embodiment employed ultrasound for the generation of thermal waves, it will be understood that in other example embodiments, ultrasound detection may be employed, and the resulting detected ultrasonic signal data may be processed according to the cross-correlation methods disclosed herein. In one example implementation, a pulsed laser may be employed to direct a chirped pulse train onto the sample and thereby generate photoacoustic ultrasonic waves in addition to photothermal radiation. Such an example embodiment may be referred to as truncated correlation photoacoustic coherence tomography (eTC-PACT).

Figure 8B:
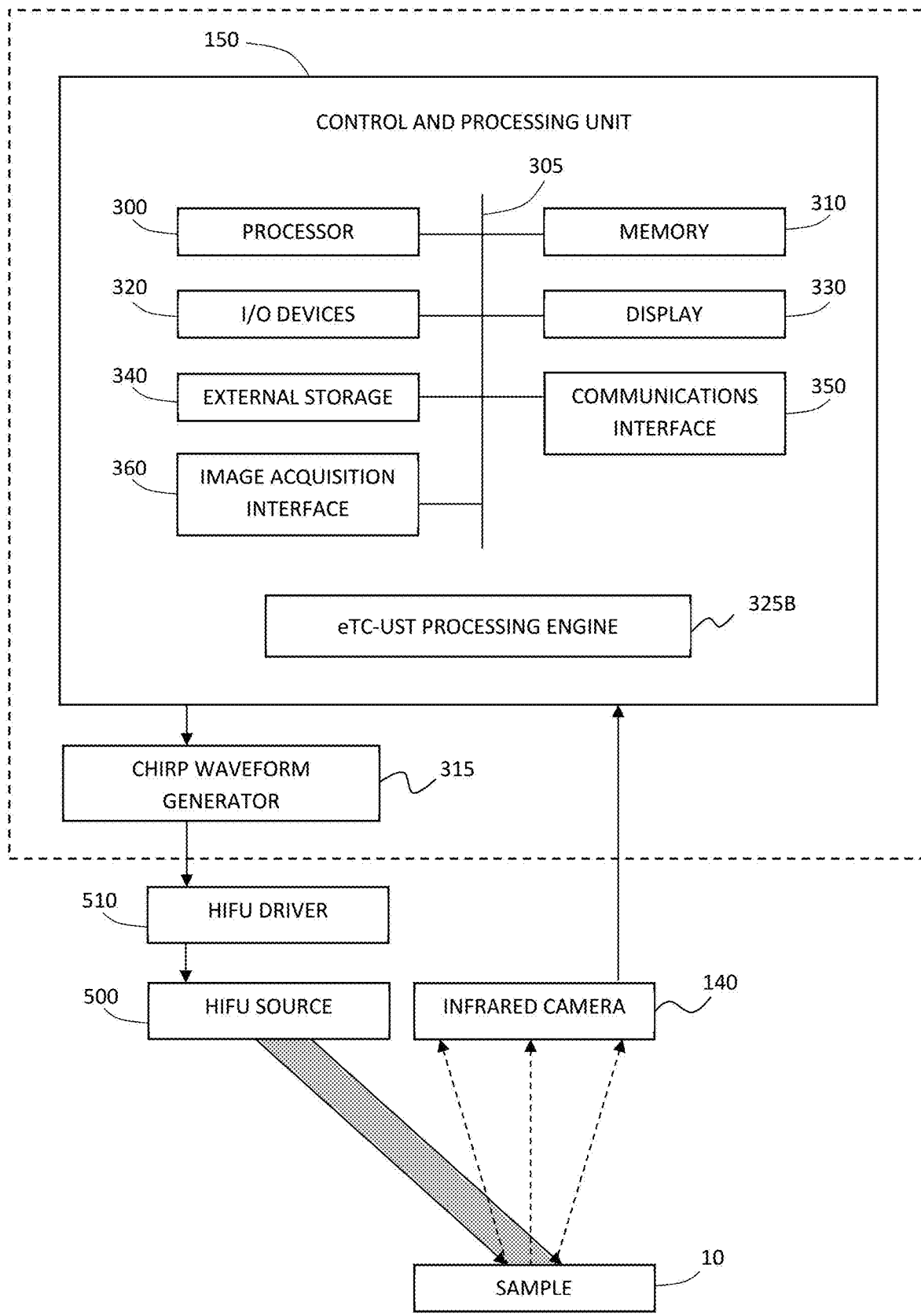

An example implementation of such an embodiment is illustrated in FIG. 8B, which is similar to FIG. 8A, but where the laser 100 (and associated driver 110) has been replaced by high-frequency ultrasound (HIFU) source 500 (e.g. with a bandwidth of approximately 1-5 MHz) and associated driver 510. HIFU source 500 emits a focused pulsed-ultrasound chirped train of pulses, in a manner similar to the emission of the chirped train of laser pulses emitted by laser 100 in FIG. 1D. HIFU source 100 is therefore employed as a heating source of controllable penetration depth and exposure area (for example, power-limited high intensity focused ultrasound). As in the photothermal embodiments, the resulting thermal infrared radiation is measured using infrared camera 140, and the acousto-thermal signal data received from infrared camera 140 is processed according to the embodiments described above, e.g. via eTC-UST processing engine 325B (UST=ultrasound tomography), where one or more truncated chirped reference waveforms are cross-correlated with the acousto-thermal signal data in order to obtain depth-resolved image data. One potential benefit of this approach is that optical scattering effects are avoided. This arrangement generates a thermal transient after each pulse of the chirped ultrasound pulse train that is processed following a method based on FIGS. 2A and 2B).

Figure 8C:
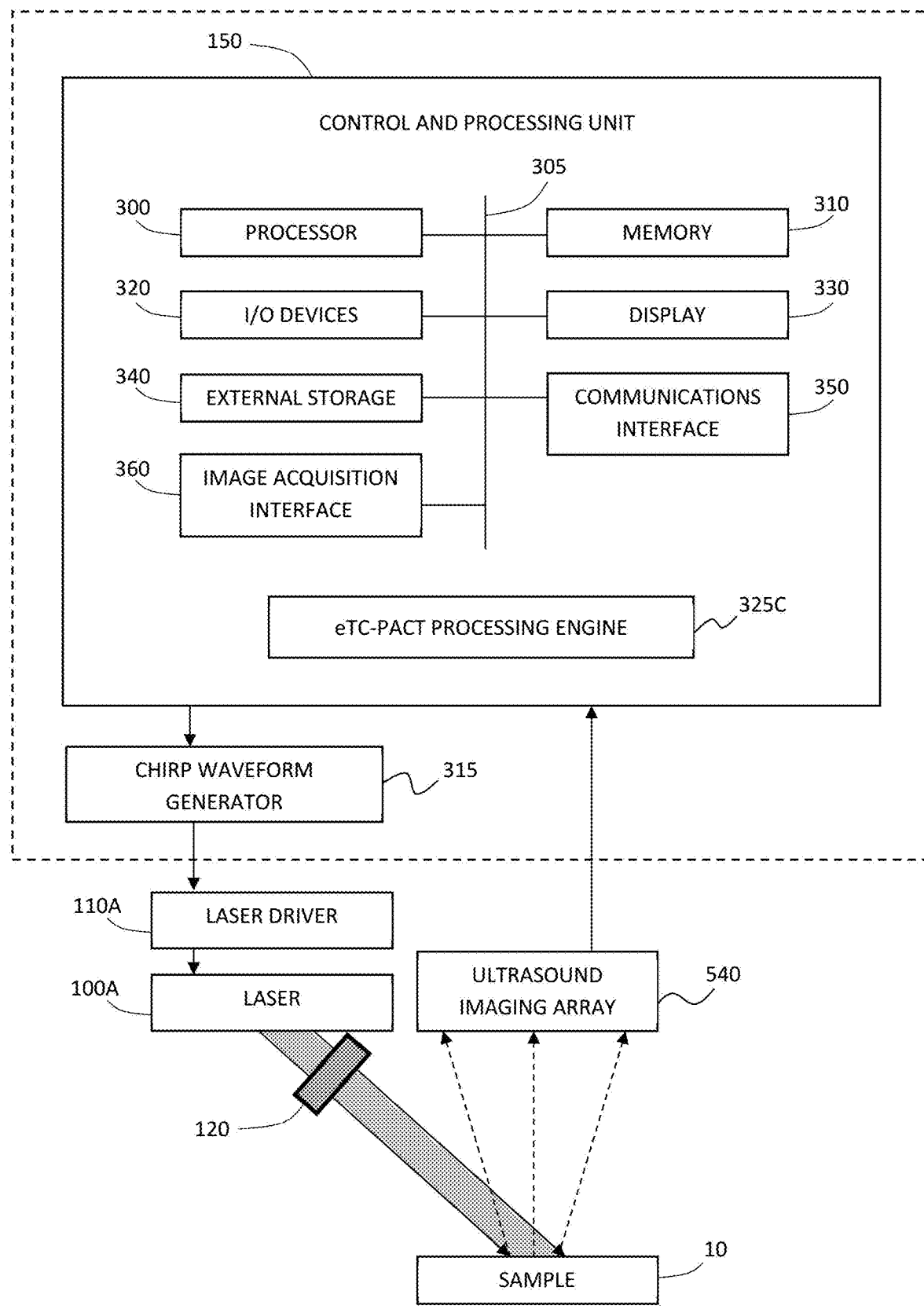

FIG. 8C illustrates an example eTC-PACT system, in which the infrared detector 140 of FIG. 8A has been replaced with an ultrasonic imaging array 540. Such an ultrasonic imaging array may for formed from a plurality of ultrasonic imaging elements have a bandwidth in the range of approximately 1-10 MHz. Laser 100A (driven by laser source 110A) may have a fixed pulse width on the nanosecond scale, for example, between approximately 10 and 100 ns, or for example, between approximately 25 and 75 ns, or, for example between approximately 40 and 60 ns. Laser source 100A generates, through optical absorption, the emission of ultrasound waves, resulting in the emission of an ultrasonic relaxation transient following the laser pulse. Cross-correlation of the detected ultrasound waves with one or more truncated reference chirped waveforms is performed, in a manner similar to that described in FIGS. 2A and 2B, e.g. via eTC-PACT processing engine 325C. While the waveforms occur on a much more rapid timescale than the waveforms of photothermal implementations, their processing can nonetheless be implemented using control and processing circuitry 150 that is equipped with suitable frame detection hardware, such as using hardware available from National Instruments.

The following examples are presented to enable those skilled in the art to understand and to practice embodiments of the present disclosure. They should not be considered as a limitation on the scope of the disclosure, but merely as being illustrative and representative thereof.

EXAMPLES

Example 1: Early Tumor Detection in a Mouse Thigh

The eTC-PCT method was applied for early in-vivo tumor detection in the thigh of a nude mouse. It exhibited high TP contrast that allowed precise measurements of very early tumor size and shape. The experimental results were validated following histological analysis from hematoxylin and eosin staining. Very early (3-day) 3D mouse thigh tumor growth eTC-PCT images were initially obtained. eTC-PCT tomographic images are sensitive to the presence of the increased angiogenetic blood vascular network in the tumor, since blood has higher absorption coefficient than the surrounding tissue in NIR excitation wavelengths, leading to high contrast tumor imaging. Additionally, TP contrast amplification occurs because the tumor has higher density and therefore smaller thermal diffusivity than the muscular tissue.

For tumor imaging, cancerous cells were injected into the right thigh of a mouse and the evolution of tumor is studied within the thigh. Imaging of the thigh was performed before the injection of the cancer cells, and subsequently, three and nine days after the injection. Afterwards, the mouse was euthanized and the leg skin was removed. The tumorous tissue was collected then and sent to Princess Margaret Hospital, Toronto, ON, for histopathology analysis. A photograph of the position of a mouse placed on the holder, during the imaging experiment, is provided in FIG. 7A. To confirm the presence of the tumor in the thigh of the mouse, histological validation was performed, as shown in FIG. 7B. The removed tumor tissue was viewed under a microscope. The tumor size and shape could be identified and were measured from the images. While the tumorous tissue reveals a high density of cancer cells that possess dark nuclei, normal tissue is seen as the pink sections.

The 3D results based on the amplitude channel can be seen in the mouse thigh before and after injection are shown in FIGS. 8A-8F. The tissue change can be seen with eTC-PCT by the third day after injecting the cancer cells. Images taken on Day 3 clearly show that the tissue structure of the thigh has changed: The tumor has been building its own vascular network to provide oxygen and nutritional support to the affected cells, therefore, more blood vessels are generated and observed in the middle area of the thigh, where the tumor is developing. More detail becomes apparent on Day 9, where the presence of a palpable mass is evident with further growth and deep subsurface penetration of the tumor. Furthermore, the tumor has higher density than muscular tissues, which changes the thermal properties of the tissue and generates additional contrast ("contrast amplification") beyond that due to optical property changes in the TP image.

Figure 9A:
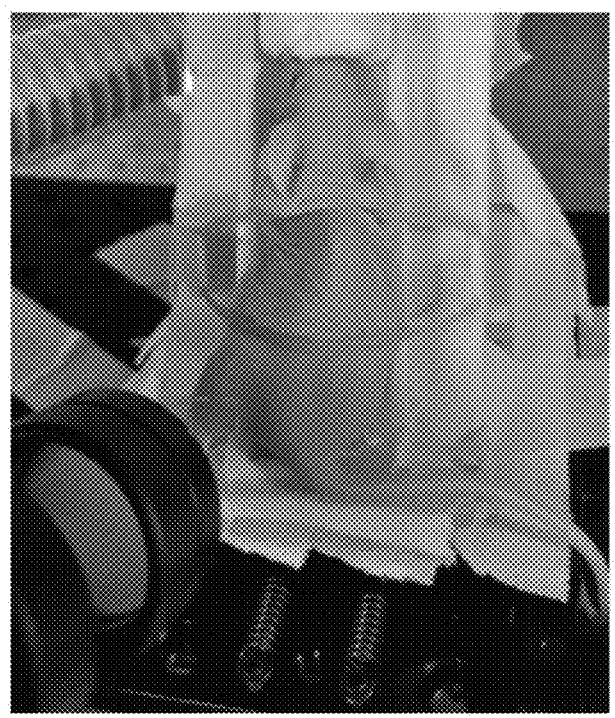
FIG. 9A is a photograph of a mouse under an anesthetic machine. The red contour shows the imaging area on the mouse thigh.
Figure 9B:
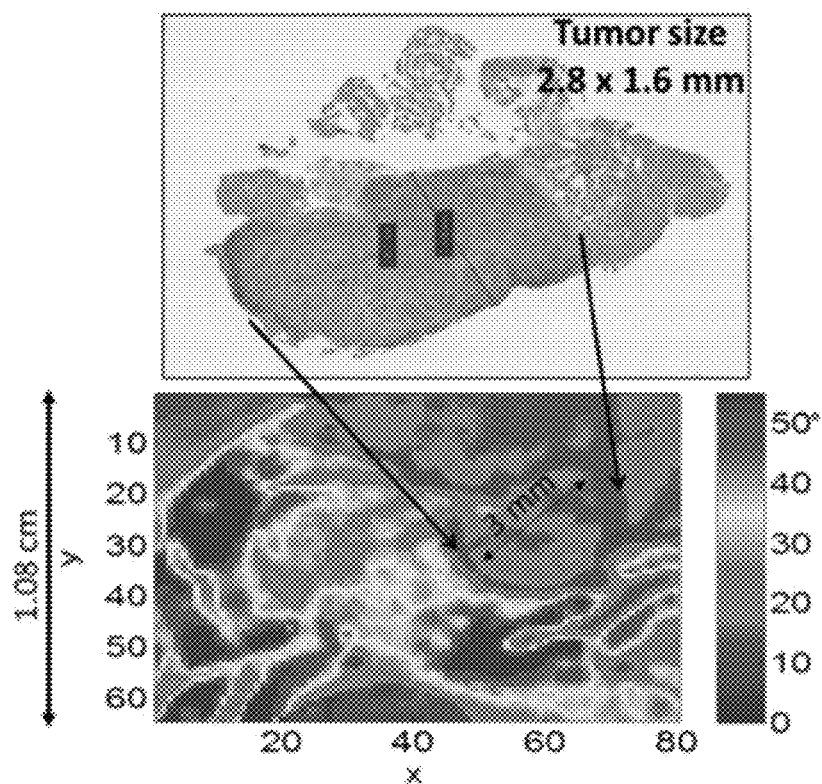
FIG. 9B shows histological validation results and comparison with the inspected phase eTC-PCT image.

The spatial-gradient-gate adaptive filter described above was applied to the tumor imaging data. Side by side amplitude and phase images of the thigh of a mouse (9 days after injection of cancer cells) along with the filtered image is presented in FIGS. 9A-9C. As a result of filtering, measurable improvement of the tumor images in FIGS. 9A and 9B can be observed in FIG. 9C with more details, finer and deeper vessels becoming visible with higher spatial resolution. The experimental pulsed chirp parameters were: Starting frequency 0.07 Hz, ending frequency 0.1 Hz, and chirp duration 81 s. Homogenized laser beam diameter was 3 cm with the excitation pulse width of 70 ms, resulting in energy density of 0.79 J/cm$^2$.

Example 2: Thermophotonic Structural Mouse Brain Imaging

Figure 10A:
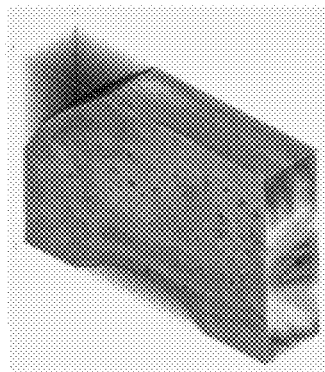
FIGS. 10A-10F show the three-dimensional image results from the from tumor growth imaging with the eTC-PCT method.
Figure 10B:
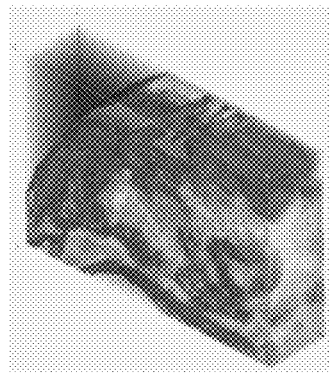
Figure 10C:
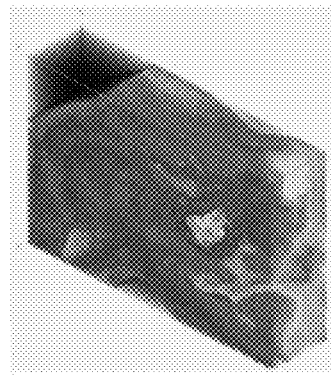
Figure 10D:
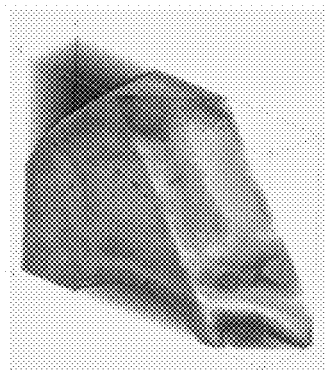
Figure 10E:
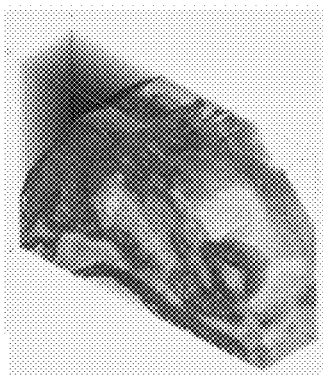
Figure 10F:
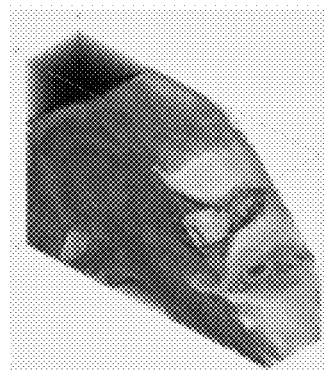
Figure 11A:
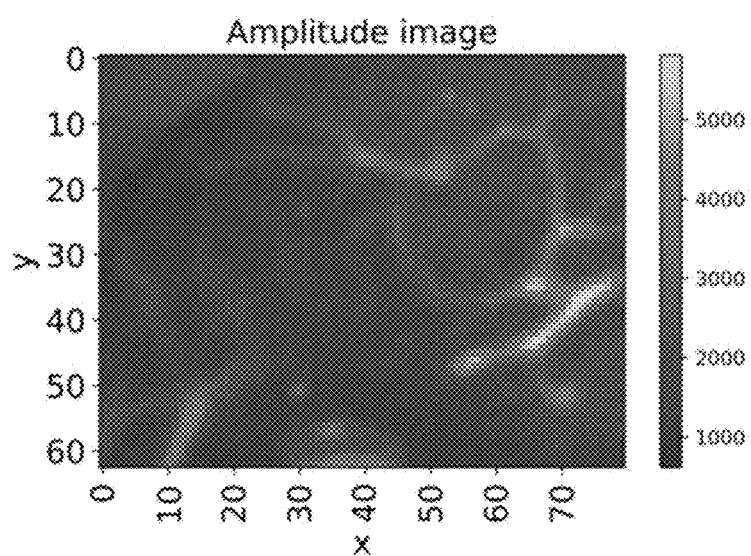
FIGS. 11A-11C show results obtained using spatial-gradient-gate adaptive filtering.
Figure 11B:
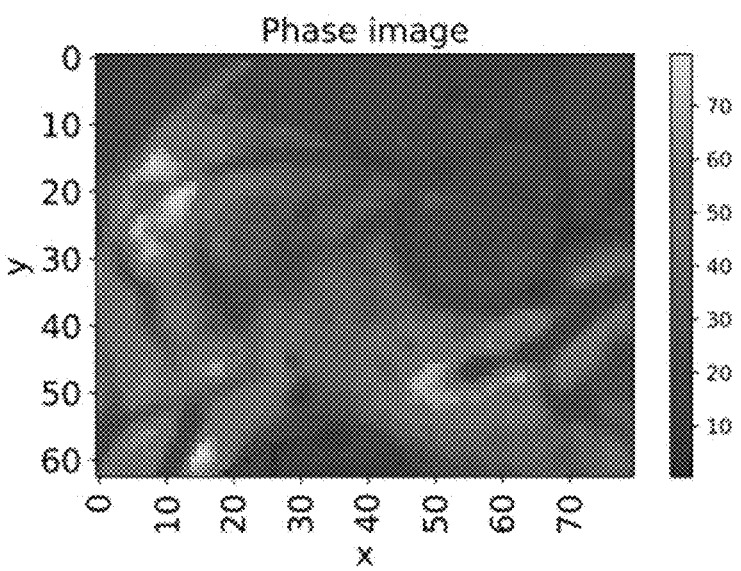
Figure 11C:
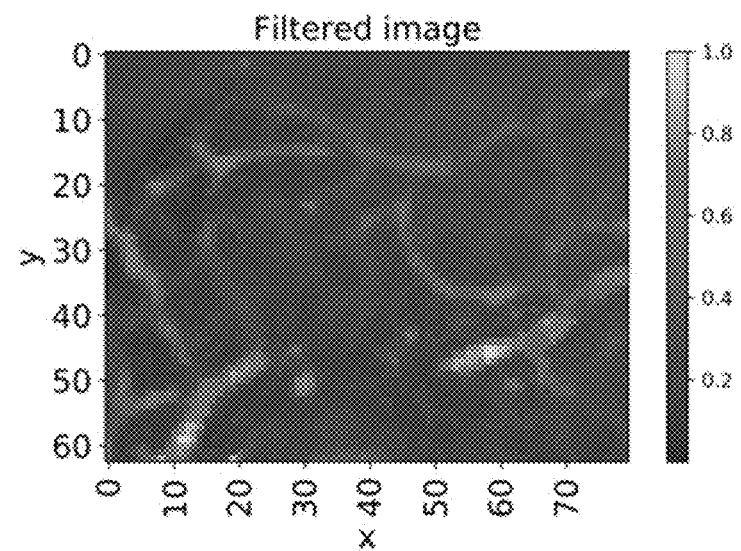
Figure 12A:
FIG. 12A is a photograph of a mouse under anesthesia.
Figure 12B:
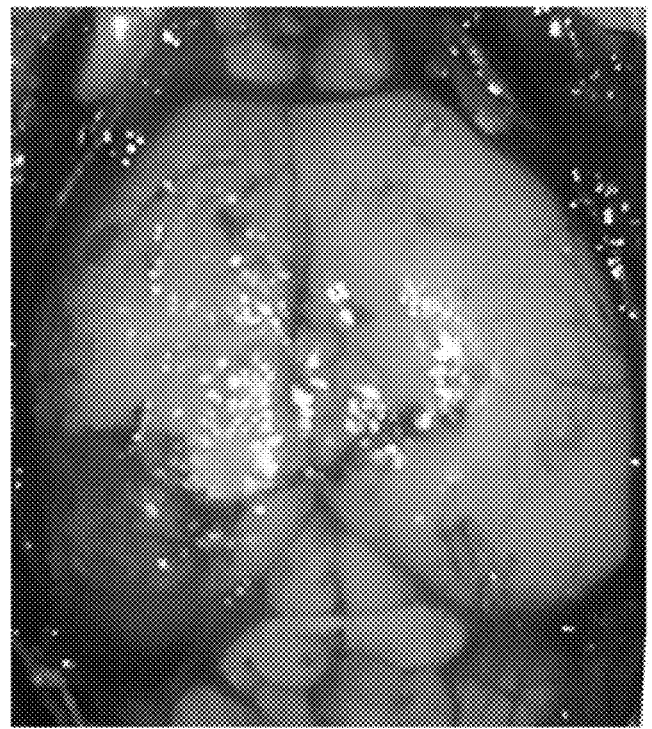
FIG. 12B is an open-skull visible-light photograph of the cortex vasculature of a euthanized mouse.
Figure 12C:
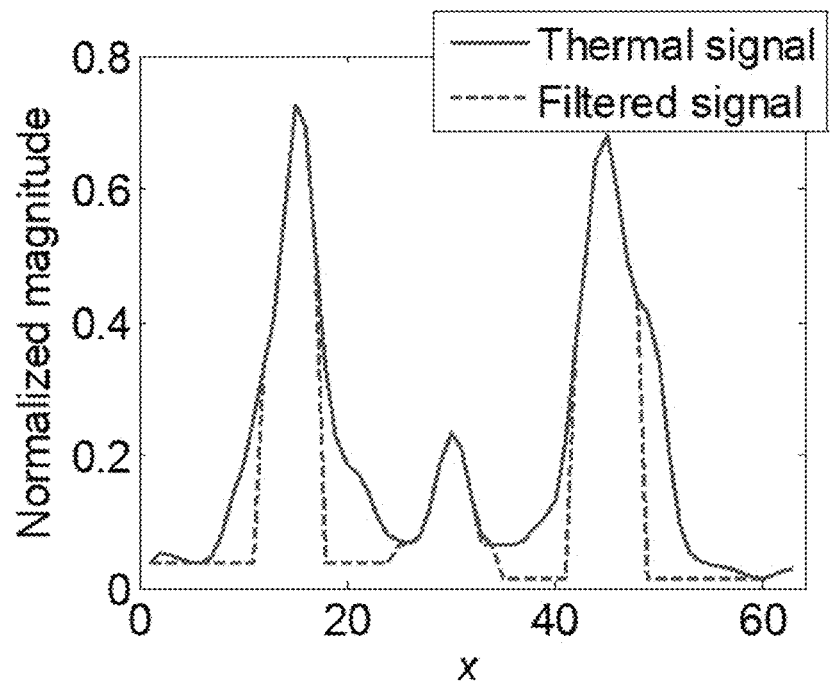
FIG. 12C displays an example of a spatial-gradient-gate adaptive filtered eTC-PCT signal (in red) of the thermally broadened absorption (in blue) along the x coordinates.
Figure 12D:
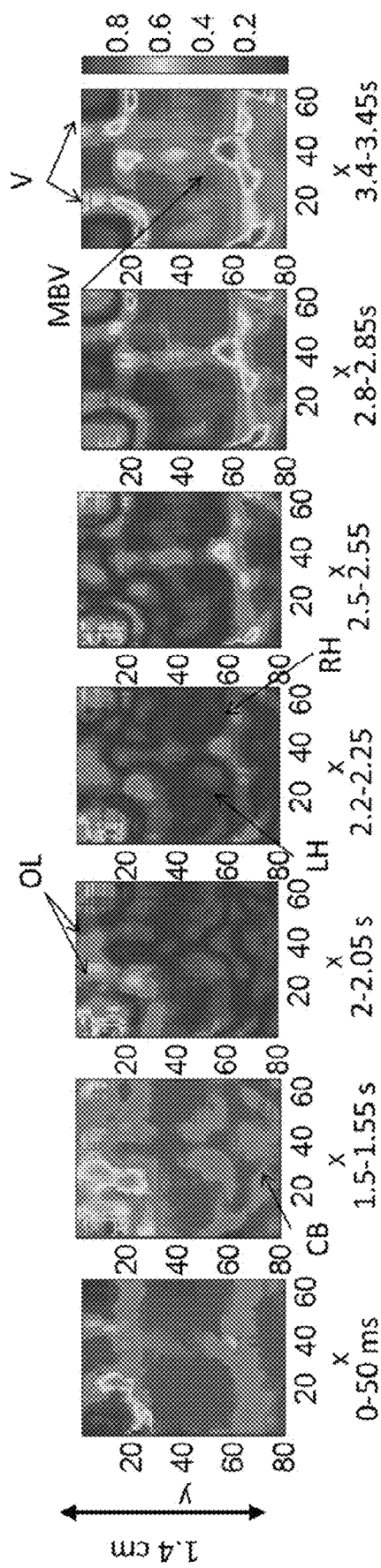
FIGS. 12D and 12E plot in-vivo non-invasive images obtained when the mouse was asleep under the anesthetic machine (D) and images obtained in the absence of the skin that were captured after the mouse was euthanized (E).
Figure 12E:
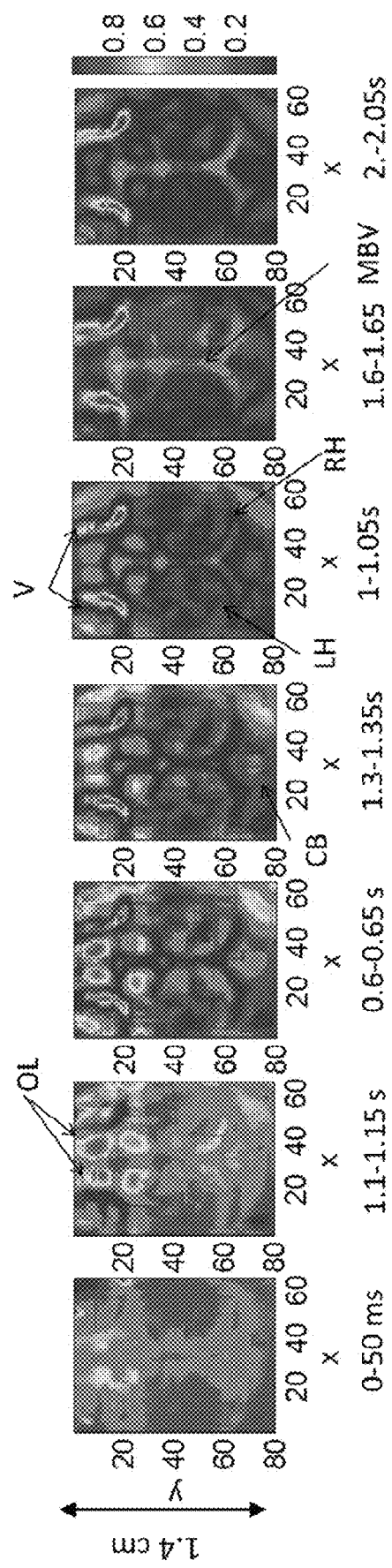

TP imaging of the brain of a live mouse was achieved noninvasively with the skin and skull intact. The mouse was placed under anesthesia as the first step and for the duration of each experiment, FIG. 10A, followed by eTC-PCT imaging of the brain. Then, the mouse was euthanized and further imaging of the brain was performed after removal of the scalp. An open-skull visible-light photograph of the cortex vasculature of the euthanized mice, FIG. 10B, was produced. The combined thickness of the skin and skull of the adult mouse covering the brain was measured to be ~0.95 mm. FIG. 10C displays an example of a filtered signal (in red) of the thermally broadened absorption (in blue) along the x coordinates (from pixel 1 to 64 at y=5, and at the depth location corresponding to t=50 ms). This algorithm is applied to the sequence of broadened features along both the x and the y axes leading to two filtered images. The two computed images were then averaged. The TP image resolution restoration filter was applied to the mixed eTC-PCT amplitude and phase images. The mixed images were obtained by multiplying the amplitude and phase results at each pixel, providing details of both channels in one. Brain imaging results are presented for two cases. First, in-vivo non-invasive images were captured when the mouse was asleep under the anesthetic machine, as shown in FIG. 11A. Next, images in the absence of the skin were captured after the mouse was euthanized, as shown in FIG. 11B. These cross-sectional images correspond to images of the superficial cortex (starting at 0 ms) and interior brain structures (up to 3.45 s) from the dorsal to the ventral part of the brain.

The experimental pulsed chirp parameters were: Starting frequency 0.03 Hz, ending frequency 0.1 Hz, and chirp duration 81 s. Homogenized laser beam diameter was 3.6 cm with the excitation pulse width of 140 ms, resulting in energy density of 1.1 J/cm2. The laser energy was less than the maximum permissible exposure, which is a useful feature toward clinical applications of the eTC-PCT technique.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing photothermal imaging, the method comprising:
    employing an excitation chirped waveform to generate a chirped sequence of optical pulses;
    a) directing the chirped sequence of optical pulses onto a sample;
    b) detecting, with an infrared camera, photothermal radiation emitted from the sample, thereby obtaining time-dependent photothermal signal data for each image pixel of the infrared camera;
    c) employing the excitation chirped waveform to provide a reference chirped waveform, the reference chirped waveform comprising a chirped sequence of pulses, wherein each pulse of the reference chirped waveform is delayed by a time delay relative to a corresponding pulse of the excitation chirped waveform;
    d) for each pixel of a plurality of pixels of the infrared camera:
        cross-correlating a respective time-dependent photothermal signal data with the reference chirped waveform and obtaining respective time-dependent cross-correlation data; and
        after having performed the cross-correlation, processing a truncated, time-gated subset of the time-dependent cross-correlation data to generate a cross-correlation measure; and
    e) generating image data based on the cross-correlation measures associated with the plurality of pixels.

2. The method according to claim 1 wherein the reference chirped waveform comprises pulses having a fixed pulse width and a chirped pulse repetition rate.

3. The method according to claim 1 wherein cross-correlation is performed based on in-phase and quadrature representations of the reference chirped waveform.

4. The method according to claim 3 wherein a temporal duration of the time-gated subset of the time-dependent cross-correlation data is equal to a difference between a temporal width of a final pulse of the time-dependent photothermal signal data and the time delay.

5. The method according to claim 1 wherein the cross-correlation measure corresponds to a peak of a time-dependent amplitude of the time-gated subset of the time-dependent cross-correlation data.

6. The method according to claim 5 wherein the cross-correlation measure comprises one or more of peak amplitude, phase value associated with the peak amplitude, and time value associated with the peak amplitude.

7. The method according to claim 1 wherein the cross-correlation measure is a phase delay corresponding to a time duration associated with a change in a sign of the phase.

8. The method according to claim 1 further comprising:
    varying a wavelength of the chirped sequence of optical pulses; and
    repeating steps a) to c) to generate multispectral image data.

9. The method according to claim 1 further comprising:
    cross-correlating the time-dependent photothermal signal data with one or more additional reference chirped waveforms, each additional reference chirped waveform having a different associated time delay applied thereto;
    generating additional image data respectively corresponding to each additional reference chirped waveform; and
    generating volumetric image data based on the image data and the additional image data.

10. The method according to claim 1 wherein each pulse of the reference chirped waveform has a pulse width less than a pulse width of the pulses of the excitation chirped waveform.

11. The method according to claim 1 wherein each pulse of the reference chirped waveform has a pulse width exceeding than a pulse width of the pulses of the excitation chirped waveform.

12. The method according to claim 1 wherein each pulse of the reference chirped waveform has a pulse width that is the same as a pulse width of the pulses of the excitation chirped waveform.

13. The method according to claim 1, further comprising:
    scanning a resonant gate filter relative to the image data, the resonant gate filter producing a peak when a spatial width of a spatial gate matches a steepest lateral gradient within an absorbing region of the image data; and
    generating a filtered image according to locations of the identified peaks;
    thereby performing adaptive spatially filtering of the image data.

14. The method according to claim 13 wherein a first filtered image is generated by scanning the resonant gate filter across a first direction, a second filtered image is generated by scanning the resonant gate filter across a second direction, and a composite filtered image is generated based on the first filtered image and the second filtered image.

15. A system for performing photothermal imaging, the system comprising:
    a laser;
    an infrared camera; and
    computer hardware comprising at least one processor and associated memory, the memory comprising instructions executable by said at least one processor to perform operations comprising:
        generating an excitation chirped waveform comprising a chirped sequence of pulses;
        controlling the laser according to the excitation chirped waveform, such that the laser emits a chirped sequence of laser pulses onto a sample;
        detecting, with the infrared camera, photothermal radiation emitted from the sample, thereby obtaining time-dependent photothermal signal data for each image pixel of the infrared camera;
        employing the excitation chirped waveform to provide a reference chirped waveform, the reference chirped waveform comprising a chirped sequence of pulses, wherein each pulse of the reference chirped waveform is delayed by a time delay relative to a corresponding pulse of the excitation chirped waveform;

for each pixel of a plurality of pixels of the infrared camera:
  cross-correlating a respective time-dependent photothermal signal data with the reference chirped waveform and obtaining respective time-dependent cross-correlation data; and
  after having performed the cross-correlation, processing a time-gated subset of the time-dependent cross-correlation data to generate a cross-correlation measure; and generating image data based on the cross-correlation measures associated with the plurality of pixels.

* * * * *